US012672935B2

(12) United States Patent (10) Patent No.: US 12,672,935 B2
Mayes et al. (45) Date of Patent: Jul. 7, 2026

(54) MARKER MATERIALS AND FORMS FOR MAGNETIC MARKER LOCALIZATION (MML)

(71) Applicant: ENDOMAGNETICS LTD, Cambridge (GB)

(72) Inventors: Eric Mayes, Cambridge (GB); Quentin John Harmer, Cambridge (GB); Kevin Lorimer, Cambridge (GB); Quentin Andrew Pankhurst, Cambridge (GB)

(73) Assignee: ENDOMAGNETICS LTD (GB)

( * ) Notice: Subject to any disclaimer, the term of this patent is extended or adjusted under 35 U.S.C. 154(b) by 58 days.

(21) Appl. No.: 18/948,054

(22) Filed: Nov. 14, 2024

(65) Prior Publication Data

US 2025/0064548 A1 Feb. 27, 2025

Related U.S. Application Data

(63) Continuation of application No. 17/988,146, filed on Nov. 16, 2022, now Pat. No. 12,161,513, which is a
(Continued)

(51) Int. Cl.
*A61B 90/00* (2016.01)
*A61B 5/00* (2006.01)
(Continued)

(52) U.S. Cl.
CPC ............... *A61B 90/39* (2016.02); *A61B 5/05* (2013.01); *A61B 5/4312* (2013.01);
(Continued)

(58) Field of Classification Search
CPC ......... A61B 90/39; A61B 5/05; A61B 5/4312; A61B 2017/00862; A61B 2090/3908;
(Continued)

(56) References Cited

U.S. PATENT DOCUMENTS 2,614,164 A 10/1952 Huston
3,445,928 A 5/1969 Beynon
(Continued)

FOREIGN PATENT DOCUMENTS

CN 101087556 12/2007
CN 104105456 10/2014
(Continued)

OTHER PUBLICATIONS

English translation of Office Action for Japanese Patent Application No. 2008-508306, dispatched in Nov. 8, 2011, 6 pages.
(Continued)

*Primary Examiner* — Bo Joseph Peng
(74) *Attorney, Agent, or Firm* — K&L GATES LLP

(57) ABSTRACT

A magnetic marker for marking a site in tissue in the body. In one embodiment, the marker comprises a magnetic metallic glass. In another embodiment, the marker is in a non-spherical configuration having an anisotropy ratio less than 9. In yet another embodiment, the marker is in a non-spherical configuration having an anisotropy ratio less than 6. In yet another embodiment, the marker is in a non-spherical configuration having an anisotropy ratio less than 3.

19 Claims, 21 Drawing Sheets

Related U.S. Application Data continuation of application No. 16/688,318, filed on Nov. 19, 2019, now Pat. No. 11,504,207, which is a continuation of application No. 15/172,187, filed on Jun. 3, 2016, now Pat. No. 10,595,957.

(60) Provisional application No. 62/170,768, filed on Jun. 4, 2015.

(51) Int. Cl.
*A61B 5/05* (2021.01)
*A61B 17/00* (2006.01)

(52) U.S. Cl.
CPC .............. *A61B 2017/00862* (2013.01); *A61B 2090/3908* (2016.02); *A61B 2090/3925* (2016.02); *A61B 2090/3954* (2016.02); *A61B 2090/3966* (2016.02); *A61B 2090/3987* (2016.02); *A61B 2090/3995* (2016.02); *A61B 2562/0223* (2013.01)

(58) Field of Classification Search
CPC .... A61B 2090/3925; A61B 2090/3954; A61B 2090/3966; A61B 2090/3987; A61B 2090/3995; A61B 2562/0223; H01F 1/032; H01F 1/12
See application file for complete search history.

(56) References Cited

U.S. PATENT DOCUMENTS

| | | | |
|---|---|---|---|
| 3,449,662 A | | 6/1969 | Wood |
| 3,492,566 A | | 1/1970 | Gross |
| 4,324,255 A | | 4/1982 | Branch et al. |
| 4,823,113 A | * | 4/1989 | Hasegawa .......... G08B 13/2417 |
| | | | 148/403 |
| 4,825,162 A | | 4/1989 | Roemer et al. |
| 4,983,912 A | | 1/1991 | Roehrlein et al. |
| 5,005,001 A | | 4/1991 | Cordery |
| 5,055,288 A | | 10/1991 | Lewis et al. |
| 5,184,070 A | | 2/1993 | Besendorfer et al. |
| 5,261,403 A | | 11/1993 | Saito et al. |
| 5,293,119 A | | 3/1994 | Podney |
| 5,313,192 A | * | 5/1994 | Ho .......................... G01V 15/00 |
| | | | 148/108 |
| 5,363,845 A | | 11/1994 | Chowdhury et al. |
| 5,402,094 A | | 3/1995 | Enge |
| 5,414,356 A | | 5/1995 | Yoshimura et al. |
| 5,416,413 A | | 5/1995 | Leussler |
| 5,437,280 A | | 8/1995 | Hussman |
| 5,512,821 A | | 4/1996 | Ando et al. |
| 5,534,778 A | | 7/1996 | Loos et al. |
| 5,537,037 A | | 7/1996 | Otaka et al. |
| 5,657,756 A | | 8/1997 | Vrba et al. |
| 5,666,052 A | | 9/1997 | Sata |
| 5,766,572 A | | 6/1998 | Hasegawa et al. |
| 5,844,140 A | | 12/1998 | Seale |
| 5,942,209 A | | 8/1999 | Leavitt et al. |
| 5,997,473 A | | 12/1999 | Taniguchi et al. |
| 6,076,008 A | | 6/2000 | Bucholz |
| 6,082,366 A | | 7/2000 | Andrä et al. |
| 6,173,715 B1 | | 1/2001 | Sinanan et al. |
| 6,205,352 B1 | | 3/2001 | Carroll |
| 6,230,038 B1 | | 5/2001 | von Gutfeld et al. |
| 6,270,464 B1 | | 8/2001 | Fulton, III et al. |
| 6,292,678 B1 | * | 9/2001 | Hall .................. A61M 25/0127 |
| | | | 606/41 |
| 6,304,075 B1 | | 10/2001 | Cordery |
| 6,347,241 B2 | | 2/2002 | Burbank et al. |
| 6,352,682 B2 | | 3/2002 | Leavitt et al. |
| 6,356,782 B1 | | 3/2002 | Sirimanne et al. |
| 6,371,904 B1 | | 4/2002 | Sirimanne et al. |
| 6,394,965 B1 | | 5/2002 | Klein |
| 6,406,420 B1 | | 6/2002 | McCarthy et al. |

| | | | |
|---|---|---|---|
| 6,418,335 B2 | | 7/2002 | Avrin et al. |
| 6,419,847 B1 | * | 7/2002 | Toyota ................ C04B 35/2633 |
| | | | 252/62.63 |
| 6,427,081 B1 | | 7/2002 | Burbank et al. |
| 6,445,185 B1 | | 9/2002 | Damadian et al. |
| 6,549,800 B1 | | 4/2003 | Atalar et al. |
| 6,592,608 B2 | | 7/2003 | Fisher et al. |
| 6,603,308 B2 | | 8/2003 | Itozaki et al. |
| 6,614,084 B1 | * | 9/2003 | Cowburn ............... G11B 5/746 |
| | | | 365/171 |
| 6,638,913 B1 | | 10/2003 | Speck et al. |
| 6,662,040 B1 | | 12/2003 | Henrichs et al. |
| 6,662,041 B2 | | 12/2003 | Burbank et al. |
| 6,699,205 B2 | | 3/2004 | Fulton, III et al. |
| 6,725,083 B1 | | 4/2004 | Burbank et al. |
| 6,730,042 B2 | | 5/2004 | Fulton et al. |
| 6,766,186 B1 | | 7/2004 | Hoyns et al. |
| 6,815,949 B2 | | 11/2004 | Kandori et al. |
| 6,835,572 B1 | | 12/2004 | Mountford et al. |
| 6,850,065 B1 | | 2/2005 | Fujita et al. |
| 6,862,470 B2 | | 3/2005 | Burbank et al. |
| 6,889,073 B2 | | 5/2005 | Lampman et al. |
| 6,920,346 B2 | | 7/2005 | Kazandjian et al. |
| 6,949,926 B2 | | 9/2005 | Murakami et al. |
| 6,963,769 B1 | | 11/2005 | Balaban et al. |
| 6,996,433 B2 | | 2/2006 | Burbank et al. |
| 7,009,398 B2 | | 3/2006 | Hahn et al. |
| 7,044,957 B2 | | 5/2006 | Foerster et al. |
| 7,084,631 B2 | | 8/2006 | Qu et al. |
| 7,116,094 B2 | | 10/2006 | Levin et al. |
| 7,229,417 B2 | | 6/2007 | Foerster et al. |
| 7,283,868 B2 | | 10/2007 | Ko et al. |
| 7,329,414 B2 | | 2/2008 | Fisher et al. |
| 7,335,511 B2 | | 2/2008 | Mountford et al. |
| 7,386,338 B2 | | 6/2008 | Hoppel et al. |
| 7,412,275 B2 | | 8/2008 | Marinelli |
| 7,416,533 B2 | | 8/2008 | Gellman et al. |
| 7,479,784 B2 | | 1/2009 | Lee |
| 7,525,308 B2 | | 4/2009 | Tsukuda et al. |
| 7,535,363 B2 | | 5/2009 | Gisselberg et al. |
| 7,570,056 B2 | | 8/2009 | Nakabayashi et al. |
| 7,625,397 B2 | | 12/2009 | Foerster et al. |
| 7,668,582 B2 | | 2/2010 | Sirimanne et al. |
| 7,676,256 B2 | | 3/2010 | Satragno et al. |
| 7,680,524 B2 | | 3/2010 | Ogawa et al. |
| 7,689,267 B2 | | 3/2010 | Prince |
| 7,701,209 B1 | | 4/2010 | Green |
| 7,702,378 B2 | | 4/2010 | Bolan et al. |
| 7,711,407 B2 | | 5/2010 | Hughes et al. |
| 7,744,852 B2 | | 6/2010 | Chernomorsky et al. |
| 7,776,310 B2 | | 8/2010 | Kaplan |
| 7,783,336 B2 | | 8/2010 | Macfarlane et al. |
| 7,792,569 B2 | | 9/2010 | Burbank et al. |
| 7,877,133 B2 | | 1/2011 | Burbank et al. |
| 7,970,454 B2 | | 6/2011 | Jones et al. |
| 7,972,619 B2 | | 7/2011 | Fisher |
| 7,983,734 B2 | | 7/2011 | Jones et al. |
| 8,050,742 B2 | | 11/2011 | Weizman |
| 8,060,183 B2 | | 11/2011 | Leopold et al. |
| 8,062,215 B2 | | 11/2011 | Voegele et al. |
| 8,064,987 B2 | | 11/2011 | Carr, Jr. |
| 8,118,754 B1 | | 2/2012 | Flynn et al. |
| 8,137,320 B2 | | 3/2012 | Mark et al. |
| 8,174,259 B2 | | 5/2012 | Hattersley et al. |
| 8,219,182 B2 | | 7/2012 | Burbank et al. |
| 8,277,391 B2 | | 10/2012 | Foerster et al. |
| 8,280,486 B2 | | 10/2012 | Miller et al. |
| 8,292,822 B2 | | 10/2012 | Fulton et al. |
| 8,306,602 B2 | | 11/2012 | Sirimanne et al. |
| 8,320,993 B2 | | 11/2012 | Sirimanne et al. |
| 8,320,994 B2 | | 11/2012 | Sirimanne et al. |
| 8,452,375 B2 | | 5/2013 | Krag et al. |
| 8,470,294 B2 | | 6/2013 | Kaplan |
| 8,600,481 B2 | | 12/2013 | Sirimanne et al. |
| 8,626,269 B2 | | 1/2014 | Jones et al. |
| 8,718,745 B2 | | 5/2014 | Burbank et al. |
| 8,821,835 B2 | | 9/2014 | Kaplan |
| 8,880,154 B2 | | 11/2014 | Jones et al. |
| 10,595,957 B2 | * | 3/2020 | Mayes ................ A61B 5/4312 |

(56) References Cited

U.S. PATENT DOCUMENTS

| | | | |
|---|---|---|---|
| 2001/0006616 A1 | 7/2001 | Leavitt et al. | |
| 2001/0011155 A1 | 8/2001 | Rapoport | |
| 2001/0012915 A1 | 8/2001 | Avrin et al. | |
| 2001/0049481 A1 | 12/2001 | Fulton, III et al. | |
| 2002/0019595 A1 | 2/2002 | Osborne et al. | |
| 2002/0035324 A1 | 3/2002 | Sirimanne et al. | |
| 2002/0058883 A1 | 5/2002 | Fulton et al. | |
| 2002/0107437 A1 | 8/2002 | Sirimanne et al. | |
| 2002/0161298 A1 | 10/2002 | Burbank et al. | |
| 2003/0016010 A1 | 1/2003 | Kandori et al. | |
| 2003/0078493 A1 | 4/2003 | Ogawa et al. | |
| 2003/0105394 A1 | 6/2003 | Fabian et al. | |
| 2003/0141868 A1 | 7/2003 | Bajharev | |
| 2003/0192557 A1 | 10/2003 | Krag et al. | |
| 2003/0214313 A1 | 11/2003 | Omura et al. | |
| 2003/0216632 A1 | 11/2003 | McClure et al. | |
| 2004/0109823 A1 | 6/2004 | Kaplan | |
| 2004/0138552 A1* | 7/2004 | Harel | A61B 1/00158 |
| | | | 600/407 |
| 2004/0138555 A1 | 7/2004 | Krag et al. | |
| 2004/0162477 A1 | 8/2004 | Okamura et al. | |
| 2004/0204660 A1 | 10/2004 | Fulton et al. | |
| 2004/0210160 A1 | 10/2004 | Fulton et al. | |
| 2004/0236212 A1 | 11/2004 | Jones et al. | |
| 2004/0236213 A1 | 11/2004 | Jones et al. | |
| 2004/0249261 A1 | 12/2004 | Torchia et al. | |
| 2005/0033157 A1 | 2/2005 | Klein et al. | |
| 2005/0033195 A1 | 2/2005 | Fulton, III et al. | |
| 2005/0045192 A1 | 3/2005 | Fulton et al. | |
| 2005/0059881 A1 | 3/2005 | Balaban et al. | |
| 2005/0059888 A1 | 3/2005 | Sirimanne et al. | |
| 2005/0080337 A1 | 4/2005 | Sirimanne et al. | |
| 2005/0080338 A1 | 4/2005 | Sirimanne et al. | |
| 2005/0080339 A1 | 4/2005 | Sirimanne et al. | |
| 2005/0085724 A1 | 4/2005 | Sirimanne et al. | |
| 2005/0148863 A1 | 7/2005 | Okamura et al. | |
| 2006/0036159 A1 | 2/2006 | Sirimanne et al. | |
| 2006/0074295 A1 | 4/2006 | Kucharczyk et al. | |
| 2006/0079770 A1 | 4/2006 | Sirimanne et al. | |
| 2006/0079805 A1 | 4/2006 | Miller et al. | |
| 2006/0079829 A1 | 4/2006 | Fulton et al. | |
| 2006/0173283 A1 | 8/2006 | Axelsson et al. | |
| 2006/0258933 A1 | 11/2006 | Ellis et al. | |
| 2006/0270930 A1 | 11/2006 | Brasile | |
| 2006/0293581 A1 | 12/2006 | Plewes et al. | |
| 2007/0082021 A1 | 4/2007 | Bates | |
| 2007/0093726 A1 | 4/2007 | Leopold | |
| 2008/0074109 A1 | 3/2008 | Tsukada et al. | |
| 2008/0091120 A1 | 4/2008 | Fisher | |
| 2008/0097199 A1 | 4/2008 | Mullen | |
| 2008/0124281 A1* | 5/2008 | Gao | B82Y 5/00 |
| | | | 977/788 |
| 2008/0146914 A1 | 6/2008 | Polzin et al. | |
| 2008/0161848 A1 | 7/2008 | Fisher | |
| 2008/0214930 A1 | 9/2008 | Brasile | |
| 2008/0228164 A1 | 9/2008 | Nicoson et al. | |
| 2008/0275333 A1 | 11/2008 | Fain et al. | |
| 2008/0294036 A1 | 11/2008 | Hoi et al. | |
| 2009/0018439 A1 | 1/2009 | Jones et al. | |
| 2009/0024022 A1 | 1/2009 | Azar et al. | |
| 2009/0082662 A1 | 3/2009 | Israel | |
| 2009/0118611 A1 | 5/2009 | He | |
| 2009/0164161 A1 | 6/2009 | Hong et al. | |
| 2009/0201016 A1 | 8/2009 | Hattersley et al. | |
| 2010/0030149 A1 | 2/2010 | Carr, Jr. | |
| 2010/0099978 A1 | 4/2010 | Geppert et al. | |
| 2010/0125191 A1 | 5/2010 | Sahin | |
| 2010/0261946 A1 | 10/2010 | Kaplan | |
| 2010/0298698 A1 | 11/2010 | Burbank et al. | |
| 2010/0305430 A1 | 12/2010 | Troesken | |
| 2011/0021888 A1 | 1/2011 | Sing et al. | |
| 2011/0052393 A1* | 3/2011 | Ogrin | A61B 5/05 |
| | | | 310/38 |
| 2011/0054519 A1* | 3/2011 | Neuss | A61B 17/12177 |
| | | | 606/213 |

| | | | |
|---|---|---|---|
| 2011/0133730 A1 | 6/2011 | Hattersley | |
| 2011/0137154 A1 | 6/2011 | Hattersley et al. | |
| 2011/0237943 A1 | 9/2011 | Jones et al. | |
| 2012/0229130 A1 | 9/2012 | Hattersley et al. | |
| 2012/0330153 A1 | 12/2012 | Sirimanne et al. | |
| 2013/0066195 A1 | 3/2013 | Sirimanne et al. | |
| 2013/0253550 A1 | 9/2013 | Beisel et al. | |
| 2013/0280168 A1 | 10/2013 | Kaplan | |
| 2013/0310686 A1 | 11/2013 | Jones et al. | |
| 2014/0018663 A1 | 1/2014 | Harmer et al. | |
| 2014/0051996 A1 | 2/2014 | Sirimanne et al. | |
| 2014/0194741 A1 | 7/2014 | Sirimanne et al. | |
| 2014/0314679 A1 | 10/2014 | Shawcross et al. | |
| 2015/0010470 A1 | 1/2015 | Kaplan | |
| 2015/0051477 A1 | 2/2015 | Jones et al. | |
| 2015/0078535 A1 | 3/2015 | DeSena et al. | |
| 2015/0238661 A1 | 8/2015 | Kaplan | |
| 2016/0354178 A1* | 12/2016 | Mayes | A61B 90/39 |

FOREIGN PATENT DOCUMENTS

| | | |
|---|---|---|
| DE | 29724862 | 3/2005 |
| DE | 102007009016 A1 | 8/2008 |
| EP | 0126580 | 11/1984 |
| EP | 0595227 | 5/1994 |
| EP | 0663599 | 7/1995 |
| EP | 0948940 A1 | 10/1999 |
| EP | 1249207 | 10/2002 |
| EP | 0966924 | 8/2003 |
| EP | 1062911 | 8/2003 |
| EP | 1284123 | 7/2005 |
| EP | 1491147 | 3/2010 |
| EP | 2267471 | 12/2010 |
| EP | 2339343 A1 | 6/2011 |
| FR | 2689638 | 10/1993 |
| FR | 2770779 | 5/1999 |
| GB | 2109112 A | 5/1983 |
| GB | 2425610 | 1/2006 |
| GB | 2465771 A | 6/2010 |
| JP | 02-078983 | 11/1990 |
| JP | 02-281170 | 11/1990 |
| JP | 05-251774 | 9/1993 |
| JP | 06-324021 | 11/1994 |
| JP | 08-015229 | 1/1996 |
| JP | 08-248004 | 9/1996 |
| JP | 08-338864 | 12/1996 |
| JP | 10-038854 | 2/1998 |
| JP | 2003-149212 | 5/2003 |
| JP | 2005-168678 | 6/2005 |
| JP | 2006-030004 | 2/2006 |
| JP | 09-027057 | 8/2014 |
| WO | 1995004287 | 2/1995 |
| WO | 9807052 | 2/1998 |
| WO | 200038579 | 7/2000 |
| WO | 01/08578 | 2/2002 |
| WO | 0239917 A1 | 5/2002 |
| WO | 2002039917 | 5/2002 |
| WO | 2005011512 | 2/2005 |
| WO | 2006009048 | 1/2006 |
| WO | 2006022786 | 3/2006 |
| WO | 2006/067692 | 6/2006 |
| WO | 2006056739 | 6/2006 |
| WO | 2006117530 | 11/2006 |
| WO | 2007034196 A2 | 3/2007 |
| WO | 2007053533 | 5/2007 |
| WO | 2011033306 | 3/2011 |
| WO | 2011067576 | 6/2011 |
| WO | 2013/114247 | 8/2013 |
| WO | 2014/013235 A1 | 1/2014 |

OTHER PUBLICATIONS

Freitas, Jr., "Nanomedicine, vol. I: Basic Capabilities", www. nanomedicine.com/NMI/8.2.1.2.htm, Landes Bioscience, George-town, TX, 1999, 4 pages.

Reddy et al., "Preparation & Application of Magnetic hydrogel nanocomposites for protein purification and Metal Absorption",

(56) References Cited

OTHER PUBLICATIONS

International Conference on Advances in Polymer Technology, Feb. 26-27, 2010, pp. 83-97, India.

European Search Report for EP 10180206, Nov. 23, 2010, 4 pages.

Fagaly, "Squid Detection of Electronic Circuits", IEEE Transactions on Magnetics, vol. 25, No. 2, Mar. 1989; pp. 1216-1218.

Noguchi et al., "Sentinel Lymphadenectomy in Breast Cancer: Identification of Sentinel Lymph Node and Detection of Metastases", Breast Cancer Research and Treatment, vol. 53, 1999, pp. 97-104.

Kim et al., "Near Infrared Fluorescent Type II Quantum Dots for Sentinel Lymph Node Mapping", Nat Biotechnol., vol. 22(1), Jan. 2004, pp. 93-97.

Gopee et al., "Migration of Intradermally Injected Quantum Dots to Sentinel Organs in Mice", Toxicological Sciences, vol. 98(1), Apr. 2007, pp. 249-297.

Soltesz et al., "Intraoperative Sentinel Lymph Node Mapping of the Lung Using Near-Infrared Fluorescent Quantum Dots", Ann thorac. Surg., vol. 79(1), Jan. 2005, pp. 269-277 (reproduced from NUH Public Access).

Peleg et al., "Implementing Metal Detector Technology and a Navidation System in the Removal of Shrapnel", Computer Aided Surgery, vol. 14, No. 103, Dec. 2009, pp. 63-68.

Conners, "Diagnostic Uses of Metal Detectors: A Review", Int. J. Clin. Pract., vol. 59(8), Aug. 2005, Blackwell Publishing, pp. 946-949.

Cash et al., "Breast Cancers: Noninvasive Method of Preoperative Localization with Three-Dimensional US and Surface Contour Mapping", Published online before print Sep. 21, 2007, doi: 10.1148/radiol.2452060906, Nov. 2007, Radiology, 245, pp. 556-566, (downloaded on Sep. 28, 2011 from http://radiology.rsna.org/content/245/2/556.full).

Peleg et al., "Integration of Computer-Aided Navidation and Metal Detector Technology in the Removal of Shrapnel in Terror Attacks Casualties", 7th Int. Conf. Computer-Aided Orthopaedic Surgery, Heidelberg, Germany, 2007, pp. 57-60.

Gunasekera et al., "Imaging Applications of Nanotechnolgy in Cancer", Targeted Oncology, vol. 4, 2009, pp. 169-181.

PCT International Search Report and PCT Written Opinion of International Searching Authority for International Patent Application No. PCT/GB2010/002233, mailed Mar. 16, 2011, (14 pages).

Williamson S.J. et al.; "Biomagnetism"; Journal of Magnetism and Magnetic Materials; XP000574230; 1981; vol. 22; pp. 129-201.

Harnan, S.E. et al.; "Magnetic resonance for assessment of axillary lymph node status in early breast cancer: A systematic review and meta-analysis"; EJSO The Journal of Cancer Surgery; 2011; vol. 37, pp. 928-936.

Material Safety Data Sheet; Revision Date Mar. 5, 2007; Retrieved from the internet: URL:https://tools.lifetechnologies.com/content/sfs/msds/2007/11361DVIAL1:MTR-NAIV_EN.pdf [retrieved on Jun. 10, 2014]; abstract; (6 pages).

Tsay, Tzong T. et al.; "Deep Cervical Lymph Flow Following the Infusion of Mannitol in Rabbits"; Life Sciences; 1997; vol. 61, No. 19; pp. 1929-1934.

PCT International Search Report and Written Opinion from PCT Application No. PCT/GB2013/051885 dated Nov. 14, 2013, 18 pages.

Jakub et al., Current status of radioactive seed for localization of non palpable breast lesions, The American Journal of Surgery, Apr. 2010, vol. 199 No. 4, pp. 522-528.

Meenach, "Synthesis and Characterization of Magnetic Hydrogel Nanocomposites for Cancer Therapy Applications," 2010, Doctoral Dissertations, Paper 108, http://uknowledge.uky.edu/gradschool_diss/108.

Postma et al., "Localization of nonpalpable breast lesions," Expert Rev. Anticancer Ther., 2011, vol. 11, No. 8, pp. 1295-1302.

Communication from corresponding EP Application No. 16728722.6 dated Apr. 29, 2019.

Groessinger et al., "Frequency Dependence of the Coercivity of Soft magnetic Materials", IEEE Transactions on Magnetics 48(4):1473-1476 (2012).

Drake; "Notes on Magnetic Measurements"; National Physical Laboratory Report; CETM; Nov. 1995; (25 pages).

Fiorillo; "Measurements of Magnetic Material"; Metrologia; 47; (2010); S114-S142; (29 pages).

BS EN 60404-7; "Method of measurement of the coercivity of magnetic materials in an open magnetic circuit"; BSI Group Headquarters; Part 7; (2016); (19 pages).

BS EN 10330:2015; "Magnetic materials—Method of measurement of the coercivity of magnetic materials in an open magnetic circuit"; BSI Standards Publication; (2015); (16 pages).

PCT International Search Report and PCT Written Opinion of International Searching Authority for International Patent Application No. PCT/GB2016/051649, mailed Nov. 25, (19 pages).

Gubin, S.P. et al., "Magnetic nanoparticles: preparation, structure and properties", Russian Chemical Reviews, (2005), pp. 489-520.

Issa, Bashar et al., Magnetic Nanoparticles: Surface Effects and Properties Related to Biomedicine Applications:, International Journal of Medical Sciences, vol. 14, (2016), pp. 21266-21305.

Anonymous: "Coercivity—Wikipedia", Jul. 8, 2015 (Jul. 8, 2015), XP055334649, Retrieved from the Internet: URL: https://en.wikipedia.org/w/index.php?t itle=Coercivity&oldid=670537509 [retrieved on Jan. 12, 2017].

Anonymous: "Magnetic susceptibility—Wikipedia", Dec. 8, 2022 (Dec. 8, 2022), XP093006269, Retrieved from the Internet: URL:https://en.wikipedia.org/wiki/Magnetic _susceptibility [retrieved on Dec. 8, 2022] (5 pages).

Vazquez, M., et al., "A Soft Magnetic Wire for Sensor Applications", Journal of Physics D: Applied Physics, Institute of Physics Publishing, Bristol, GB, vol. 29, No. 4, Apr. 14, 1996 (Apr. 14, 1996), pp. 939-949.

Reedlunn, Benjamin, et al., "Superelastic shape memory alloy cables: Part I—Isothermal tension experiments", International Journal of Solids and Structures, vol. 50, No. 20-21, Oct. 1, 2013 (Oct. 1, 2013), pp. 3009-3026.

European Search Report for Application No./Patent No. 22176363. 4-1122 / 4085866 dated Dec. 13, 2022 (18 pages).

* cited by examiner

*Magnetization curves for soft and hard magnetic material*

*Influence of marker bend angle on anisotropy ratio.*

Sample marker

Rotatable
Sample holder
(non magnetic)

Susceptometry
probe

Fixed
distance

*Test arrangement for measuring magnetic anisotropy*

A signal at a constant distance from 5mm Iron (99.5%) markers with various inclusive angles, where 180-degrees is a straight cylinder and 0-degrees is U-shaped A signal at a constant distance from 7mm multi-stand stainless steel markers with various inclusive angles, where 180-degrees is a straight cylinder and 0-degrees is U-shaped

| | Marker | Dimensional ratio length:diameter pre-deployment | Volume (mm³) | Signal Max | Signal Min | Anisotropy Ratio |
|---|---|---|---|---|---|---|
| | MnZn-Ferrite (ø0.75mm) | 10 | 3.3 | 4120 | 202 | 20.4 |
| | MnZn-Ferrite (ø1.0mm) | 3.5 | 5.9 | 981 | 166 | 5.9 |
| | Ferritic stainless steel | 3.7 | 2.1 | 3885 | 828 | 4.7 |
| | Ferritic stainless steel | 7 | 4.7 | 1518 | 148 | 10.3 |
| | Ferritic stainless steel | 11.3 | 2.7 | 1070 | 71 | 15.1 |
| | Martensitic stainless steel | 7.4 | 3.1 | 1135 | 147 | 7.7 |
| | Ferritic stainless steel multi-strand cable (ø0.91mm) | 3.3 | 2.0 | 536 | 120 | 4.5 |
| | Ferritic stainless steel multi-strand cable (ø0.91mm) | 4.4 | 2.6 | 939 | 143 | 6.6 |
| | Ferritic stainless steel multi-strand cable (ø0.91mm) (straight or 180 inclusive angle) | 5.5 | 3.3 | 1722 | 223. | 7.7 |
| | Ferritic stainless steel multi-strand cable (ø0.91mm) 135-degrees inclusive bend | 5.5 | 3.3 | 1180 | 280 | 4.2 |
| | Ferritic stainless steel multi-strand cable (ø0.91mm) with 90-degree inclusive bend | 5.5 | 3.3 | 974 | 384 | 2.5 |
| | Ferritic stainless steel multi-strand cable (ø0.91mm) with 45-degree inclusive bend | 5.5 | 3.3 | 624 | 561 | 1.1 |
| | Ferritic stainless steel multi-strand cable (ø0.91mm) in 0-degree inclusive angle (U-shape) | 5.5 | 3.3 | 624 | 354 | 1.8 |

Fig. 2(E)

| | Marker | Dimensional ratio length:diameter pre-deployment | Volume (mm³) | Signal Max | Signal Min | Anisotropy Ratio |
|---|---|---|---|---|---|---|
| | Ferritic stainless steel multi-strand cable (ø0.91mm) | 7.7 | 4.6 | 3660 | 356 | 10.3 |
| | Ferritic stainless steel multi-strand cable (ø0.91mm x 6mm) in U-shape | 6.6 | 3.9 | 846 | 395 | 2.1 |
| | Two (2) Ferritic stainless steel multi-strand cable various configurations | 6.6 (2 x 3.3) | 3.9 | 810-1091 | 240-254 | 3.2-4.6 |
| | Fe (99.5%) ø1.0mm straight or 180-degree inclusive angle | 5 | 3.9 | 2535 | 321 | 7.9 |
| | Fe (99.5%) ø1.0mm straight or 180-degree inclusive angle | 7 | 5.5 | 3721 | 417 | 8.9 |
| | Fe (99.5%) ø1.0mm 135-degrees inclusive bend | 7 | 5.5 | 2980 | 594 | 5.0 |
| | Fe (99.5%) ø1.0mm with 90-degree inclusive bend | 7 | 5.5 | 2318 | 884 | 2.6 |
| | Fe (99.5%) ø1.0mm) with 45-degree inclusive bend | 7 | 5.5 | 1499 | 1289 | 1.2 |
| | Fe (99.5%) ø1.0mm) in 0-degree inclusive angle (U-shape) | 7 | 5.5 | 1502 | 794 | 1.9 |
| | Fe (99.95%) ø0.5mm | 12 | 1.2 | 790 | 74 | 10.7 |
| | Fe (99.95%) ø0.5mm with 60-degree inclusive bend | 12 | 1.2 | 458 | 358 | 1.3 |
| | Mu Metal multistrand ø0.6mm | 8.3 | 1.4 | 1118 | 128 | 8.7 |

Fig. 2(F)

| | Marker | Dimensional ratio length:diameter pre-deployment | Volume (mm³) | Signal Max | Signal Min | Anisotropy Ratio |
|---|---|---|---|---|---|---|
| | Mu Metal multistrand ø0.6mm | 11.7 | 1.9 | 2475 | 180 | 13.7 |
| | Mu Metal multistrand ø0.6mm | 16.7 | 2.8 | 6539 | 229 | 28.5 |
| | Mu Metal multistrand ø0.6mm in 0-degree inclusive angle (U-shape) | 8.3 | 1.4 | 433 | 202 | 2.1 |
| | Dumbbell-like: Ferritic stainless steel multi-strand: large ø1.5mm for 1mm, small ø0.91, overall length 5mm | 3.3 | 4.6 | 1469 | 323 | 4.6 |
| | Ball of yarn type: Metglass ø0.125mm, final dimensions loose ball of 2.5mm | 41 | 1.0 | 1752 | 949 | 1.9 |
| | Ball of yarn type: ferritic stainless steel (ø0.3 wire), final dimensions ball of 2mm x 3mm x 4mm | 5.3 | | 1338 | 787 | 1.7 |
| | Ball of yarn type with collapsing plastic hinges: ferritic stainless steel (ø0.3 wire), overall dimensions ø1.5mm x 12mm | 8 | 21.2 | 1086 | 750 | 1.5 |
| | Ball of yarn type with collapsing hinges: ferritic stainless steel (ø0.3 wire), overall dimensions 1.5mm x 23 | 11.5 | 30.1 | 2030 | 1501 | 1.4 |
| | String of columns 3-links: MnZn-Ferrite (ø1.5) | 8 | 21.2 | 2327 | 1769 | 1.3 |
| | String of columns 4-links: MnZn-Ferrite (ø1.5) | 10.7 | 28.3 | 2707 | 2145 | 1.3 |

Fig. 2G

| | Marker | Dimensional ratio length:diameter pre-deployment | Volume (mm$^3$) | Signal Max | Signal Min | Anisotropy Ratio |
|---|---|---|---|---|---|---|
| | Collapsing chain 5-links: Fe 99.95% (ø0.5 wire), overall dimensions 2mm x 10mm | 5 | 31.4 | 1390 | 1086 | 1.3 |
| | Spring in circle: Fe 99.95% (ø0.5 wire), overall dimensions 2mm x 20mm (coil width 2mm) | 10 | 62.8 | 3990 | 3104 | 1.3 |
| | Spring in circle: Fe 99.95% (ø0.5 wire), overall dimensions 2mm x 14mm (coil width 2mm) | 7 | 44.0 | 3249 | 2305 | 1.4 |
| | Spiral in circle: Ferritic Stainless Steel (ø0.3 single wire), overall dimensions 0.91mm x 15.7mm | 17.4 | 10.8 | 772 | 251 | 3.1 |
| | Spiral in circle: Ferritic Stainless Steel (2 x ø0.3 wire), overall dimensions 0.91mm x 15.7mm | 17.4 | 10.8 | 1021 | 292 | 3.5 |
| | Spiral in circle: Ferritic Stainless Steel (2 x ø0.3 wire), overall dimensions 0.91mm x 12.6 mm | 14 | 8.7 | 785 | 261 | 3.0 |
| | Interlocked U's: Ferritic stainless steel multi-strand overall dimensions 2mm x 7mm | 3.5 | 15.9 | 5012 | 1060 | 4.7 |
| | Single U of the interlocked U's Ferritic stainless steel mullti-strand, overall dimensions 2mm x 6.5mm | 3.25 | 7.9 | 3253 | 644 | 5.1 |
| | Interlocked U's: Ferritic stainless steel mullti-strand, overall dimensions 2mm x 5.5mm | 2.75 | 12.2 | 3159 | 1045 | 3.0 |

Fig. 2(H)

| | Marker | Dimensional ratio length:diameter pre-deployment | Volume (mm³) | Signal Max | Signal Min | Anisotropy Ratio |
|---|---|---|---|---|---|---|
| | Interlocked U's: Fe (99.95%), overall dimensions 1.5mm x 4mm | 2.7 | 2.4 | 723 | 185 | 3.9 |
| | Tetrahedron from 2-columns: Fe (99.5%) each column ø1.0 x 3mm | 9 | 4.7 | 858 | 678 | 1.3 |
| | Tetrahedron from 2-columns: Ferritic stainless steel mullti-strand, each column ø0.9 x 5mm | 11 | 6.6 | 1308 | 1129 | 1.2 |
| | 3 edges of tetrahedron inclusive angle 45-degrees out of plane between edges: Ferritic stainless steel (ø0.3) | 40 | 0.8 | 342 | 231 | 1.5 |
| | 3 edges of tetrahedron inclusive angle 45-degrees out of plane between edges: Fe (99.5%) ø1.0mm | 7 | 5.5 | 875 | 734 | 1.2 |
| | 3 edges of tetrahedron inclusive angle 45-degrees out of plane between edges: Fe (99.95%) ø0.5mm | 36 | 3.5 | 1608 | 998 | 1.6 |
| | 3 edges of tetrahedron inclusive angle 45-degrees out of plane between edges: Fe (99.95%) ø0.5mm | 30 | 2.9 | 1072 | 609 | 1.8 |
| | Standard Marker Material: 316 stainless steel ø1.0mm | 6 | 4.7 | 0 | 0 | No response |
| | Standard Marker Material: Gold ø1.0mm | 3 | 2.4 | 0 | 0 | No response |

Fig. 2(I)

| | Marker | Dimensional ratio length:diameter pre-deployment | Volume (mm³) | Signal Max | Signal Min | Anisotropy Ratio |
|---|---|---|---|---|---|---|
| | SecurMark® (Titanium) | | | 0 | 0 | No response |
| | RFID ø2.1mm x 12mm | 5.7 | 41.6 | 4840 | 330 | 14.7 |
| | RFID ø1.4mm x 8mm | 5.3 | 12.3 | 1858 | 61 | 30.5 |

Fig. 2(J)

"Lozenge" or "bead" shape marker cross sections (B) and (C)

"Dumbbell-like" forms of magnetic markers

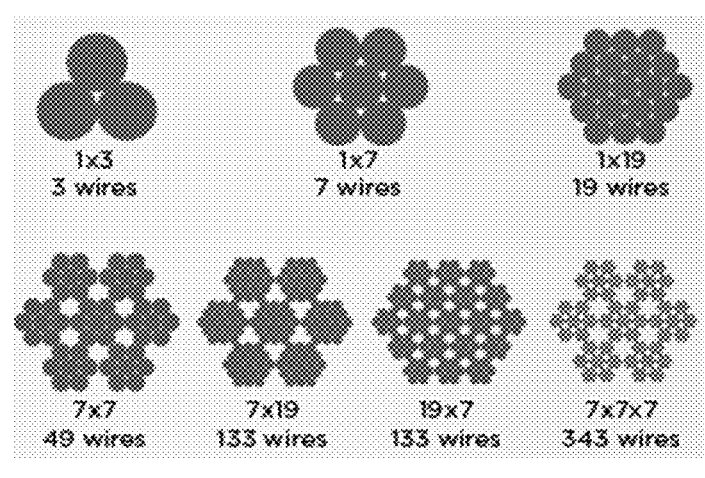
Fig. 5(A)                    Fig. 5(B)
Cross section of twisted stranded cable and hollow cable.
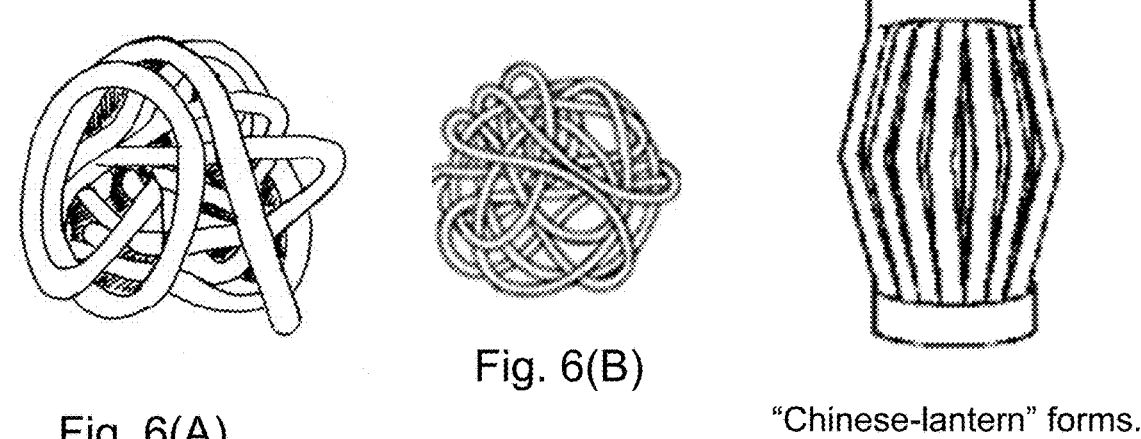
Fig. 6(B)
Fig. 6(A)                          "Chinese-lantern" forms.
Fig. 7

Marker with hinges (plastic/pre-stressed/shape memory) in same
material, more or less larger sections are possible Example alternative cross-sections for improved imaging by
increasing the number of facets.

Wire cross section with different core to sheath materials
(where one or the other is the soft or quasi-soft magnetic material)

Drawing die

Sheath material

Core material 1

Core material 2

Wire with multiple segmented core materials where at least one is soft magnetic.

Fig. 12(A)
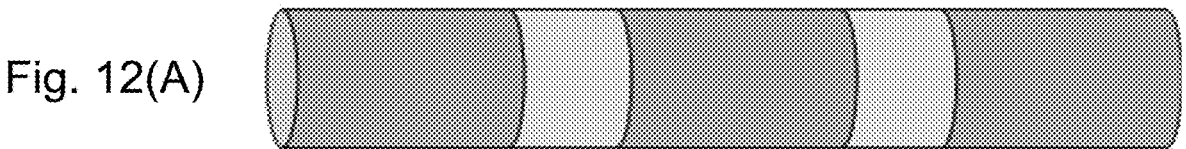
Fig. 12(B)
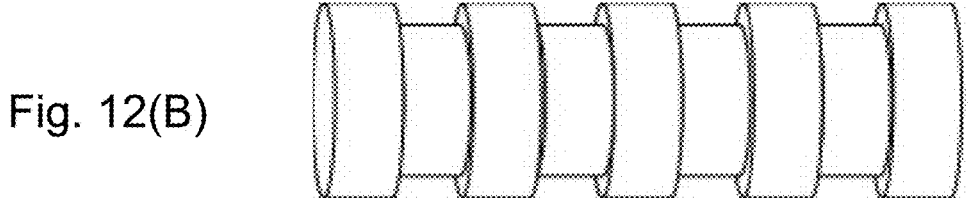
Fig. 13 (A)
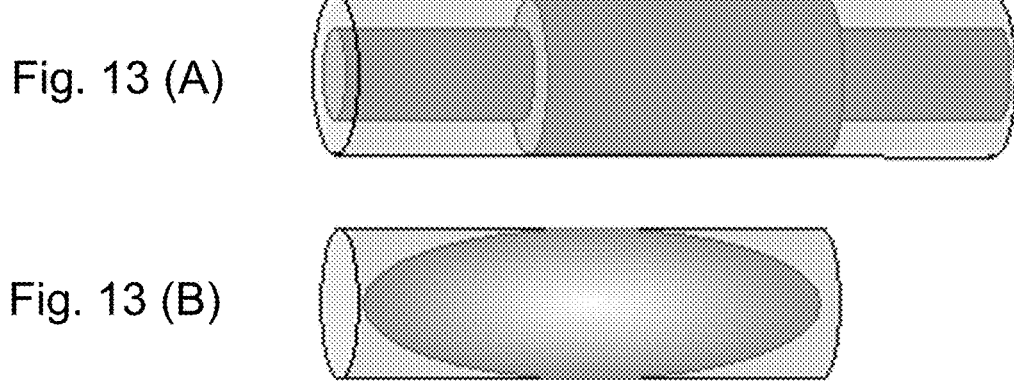
Fig. 13 (B)
Fig. 13 (C)
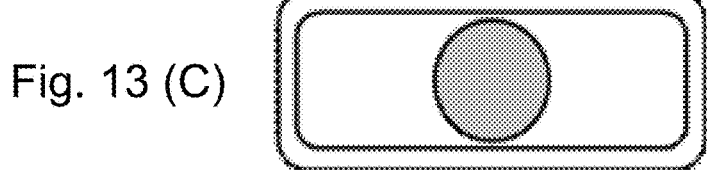

Multiple quasi-soft magnetic markers self-assembled into
an associated magnetic marker Super-hydrophobic coated markers or particles which self-assembled,
to minimise surface energy.

MARKER MATERIALS AND FORMS FOR MAGNETIC MARKER LOCALIZATION (MML)

RELATED APPLICATIONS

This application is a continuation of U.S. patent application Ser. No. 17/988,146, filed on Nov. 16, 2022, which is a continuation of U.S. patent application Ser. No. 16/688,318, filed Nov. 19, 2019, now U.S. Pat. No. 11,504,207, which is a continuation of Ser. No. 15/172,187, filed on Jun. 3, 2016, now U.S. Pat. No. 10,595,957, which claims priority to and the benefit of U.S. Provisional Application No. 62/170,768, filed Jun. 4, 2015, the entire disclosures of which are incorporated by reference herein.

FIELD OF THE INVENTION

The invention relates generally to the field of markers for medical detection and more specifically to magnetic medical markers.

BACKGROUND OF THE INVENTION

With the increasing prevalence of mammography screening programs, the majority of breast cancers are detected as small, non-palpable (or occult) lesions that are amenable to breast conserving treatment. Accurate localization of non-palpable breast cancers is key to allowing surgical removal of the complete tumor with adequate margins. If the tumor is not completely excised, patients need to undergo a further operation to remove any remaining cancerous tissue. Accurate localization also helps to avoid excision of excess breast tissue that could result in adverse cosmetic results. Accurate localization is required by other cancers such as colorectal, prostate and lung, as well as other conditions known by those of ordinary skill in this art.

The current gold standard for localization of non-palpable lesions during surgery is wire-guided localization (WGL). Although this technique is widely used, WGL has a number of disadvantages. First, it involves two separate procedures, and can present logistical and scheduling difficulties between radiology and surgery departments. Second, the positioning of the guidewire may not be optimal for achieving the desired cosmetic result in the subsequent surgery. Third, the hook wire can migrate away from the site of the lesion or become displaced during mammography or moving the patient. Fourth, the insertion of the wire can be painful for patients and finally, the risk of infection means that surgery usually needs to take place the same day as the wire insertion.

In order to overcome these disadvantages, other localization techniques have been developed. One such technique is Radioguided Occult Lesion Localization (ROLL) using a radiotracer injected into the tumor and detected by a hand-held gamma probe. Although this removes the logistical complexity of WGL, the technique introduces the drawback of the use of radioactive materials, which require special handling and disposal procedures.

Magnetic markers are also used, and they overcome the inconvenience and logistical challenges that arise by using a radioactive material as a marker, and they also avoid the drawbacks of guide-wires. However, magnetic markers are relatively complex to manufacture compared with guide-wires.

All known marking devices, including wire guides and magnetic markers, are introduced through a hollow needle or cannula. To minimize patient discomfort, this needle is typically narrow in diameter. The small diameter of the needle constrains the marker cross section. For conventional biopsy needles this dimension is generally 14 to 18 gauge. This means that the needle has an internal diameter generally of 0.8 mm to 1.5 mm but may possibly be as large as 1.8 mm for certain needle designs. If a vacuum-assisted needle is used, the needle size is typically 11 gauge, with an internal diameter of 2.3 to 2.5 mm. Thus, the magnetic markers are typically constrained to be less than 1.5 mm in diameter. In practice, these size constraints limit the magnetic response and in turn the ease with which the marker can be localised with a magnetic probe. Therefore, a stronger magnetic response is desired.

Another challenge for magnetic biopsy markers is that to achieve an effective magnetic response, the volume of material needs to be maximised. This volume requirement results in a typically shaped marker having a length significantly greater than its diameter. Such markers are in the region of 1 mm to 12 mm, with a length to diameter ratio greater than 5. This aspect ratio results in a non-uniform magnetic response with a much stronger signal being obtained when the marker major axis is in line with a probe, and a weaker signal when the marker major axis is transverse to the probe. A more uniform response is generally desired.

Further, the marker is generally guided to its position and confirmed to be in place under ultrasound or stereotactic x-ray imaging. This means that it is desirable for the marker to be clearly visible under X-ray and ultrasound imaging, and preferably under MRI, which can also be used for this purpose.

What is needed is a marker that has a small amount of material without reducing the intensity of the detectable signal, and provides a more uniform response from any direction relative to the magnetic probe.

The present invention addresses this need.

SUMMARY OF THE INVENTION

The invention relates to magnetic markers for surgical use. In particular, it relates to magnetic markers with a more uniform magnetic response once deployed than would be expected from their geometry prior to deployment.

In one aspect, markers are provided whose shape is chosen such that they give a more uniform magnetic response.

In another aspect, markers are provided whose geometrical configuration changes once deployed such that they give a more uniform magnetic response.

In another aspect, markers are provided whose material composition is chosen such that they give a more uniform magnetic response than would be expected from their geometry prior to deployment.

In one aspect, the marker is in a non-spherical configuration having a ratio of anisotropy of magnetic susceptibility of less than 9. In yet another embodiment, the marker is in a non-spherical configuration having a ratio of anisotropy of magnetic susceptibility of less than 6. In still yet another embodiment, the marker is in a non-spherical configuration having a ratio of anisotropy of magnetic susceptibility of less than 3. In one embodiment, the non-spherical marker configuration is of the shape selected from the group comprising a cylinder, a cable, a "dumbbell-like" form, a bead and a ball of yarn. In another embodiment, the cylinder bends upon placement in tissue. In yet another embodiment, the non-spherical configuration is faceted.

In one embodiment, the marker is a magnetic marker for marking a site in tissue in the body comprising: a plurality of magnetic components linked by flexible non-magnetic components that compact upon placement in the site. In another embodiment, the magnetic marker for marking a site in tissue in the body includes a magnetic component of a first shape located within a non-magnetic matrix of a second shape. In yet another embodiment, the magnetic marker for marking a site in tissue in the body includes a magnetic material core within a magnetic material sheath. In still another embodiment, one of the core and the sheath is a soft-magnetic material.

In one embodiment, the magnetic marker for marking a site in tissue in the body includes a plurality of magnetic components which self assemble into the magnetic marker following placement of the markers into the body. In another embodiment, the magnetic components are each encased within a super-hydrophobic coating. In still yet another embodiment, the magnetic marker for marking a site in tissue in the body includes a magnetic metallic glass.

BRIEF DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

FIGS. 2(E)-2(J) show an anisotropy ratio for various shapes and sizes of magnetic markers at a constant distance;

FIGS. 5(A) and (B) are diagrams of cross-sections of embodiments of the invention in cable form;

FIGS. 6(A) and 6(B) are diagrams of an embodiment of the invention in the shape of a "ball of yarn";

FIG. 7 is a diagram of an embodiment of the invention in the shape of a "Chinese lantern";

FIGS. 12(A) and (B) are diagrams of embodiments of the invention as segmented markers;

FIGS. 13(A), (B) and (C) are diagrams of embodiments of the invention in which the shape of the magnetic material and the external shape of the marker are different;

DESCRIPTION OF PREFERRED EMBODIMENTS

Figures 1A, 1B:
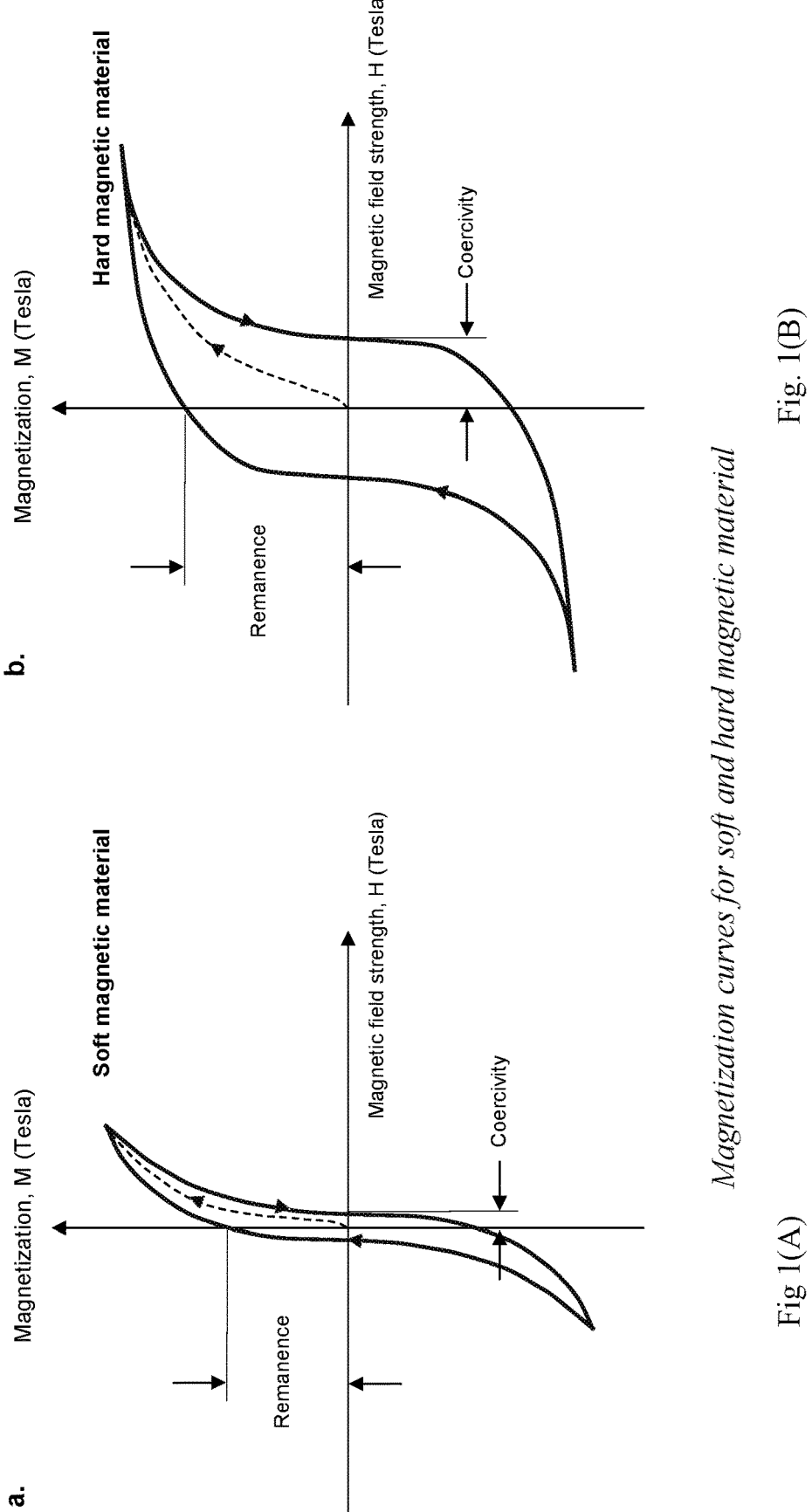
FIGS. 1(A) and (B) are magnetization curves for soft and hard magnetic material respectively.

A method for making magnetic markers as permanent magnets is described in U.S. Pat. No. 6,173,715. Permanent magnet implants have the drawback that they will attract any magnetic material in the vicinity and therefore could interact undesirably with other implants, or move in the tissue, for example, when a surgical tool made from magnetic material is nearby.

A method for making markers formed from superparamagnetic iron oxide (SPIO) nanoparticles in bioabsorbable form is described in US Publication No. 2014/0314679. SPIO particles avoid the concerns that occur for permanent magnetic markers because such materials have no magnetic remanence, and are not magnetic in themselves, but only become magnetized when in the presence of a magnetic field. The detection and localization of these SPIO magnetic markers can be performed with a sensitive magnetometer (or susceptometer) that generates an alternating magnetic field to excite the marker magnetically, and detects the magnetic field signature generated by the marker, as disclosed in US Publication No. 2011/0133730.

Another challenge for magnetic biopsy markers is that to achieve an effective magnetic response, the volume of material needs to be maximised. These requirements result in a typical marker having length significantly greater than the diameter because the marker must be delivered through a needle and smaller needle gauges (diameters) are less painful for patients. Such markers are in the region of 1 mm to 12 mm, with length to diameter ratio greater than 5. In practice, these size constraints limit the magnetic response and in turn the ease with which the marker can be localised with a magnetic probe. Therefore a stronger response is desired.

Further, the marker is generally guided to its position and confirmed to be in place under ultrasound or stereotactic x-ray imaging. This means that it is desirable for the marker to be clearly visible under X-ray and ultrasound imaging, and preferably under MRI, which can also be used for this purpose. SPIO particles have limited visibility under X-ray imaging but can be made ultrasound visible by combining them in a matrix of echogenic material, for example a polymer. Although magnetic markers overcome the drawbacks of guide-wires and radioactive approaches, there remains a need for a magnetic marker that can be introduced through a narrow needle, gives a strong magnetic response, is visible under X-ray and ultrasound imaging, and can be manufactured simply.

The requirement for the marker to be magnetically local-isable requires a certain magnetic response from the implanted material, and for this response to be measurable at a distance removed from the material. This response is related to the magnetic susceptibility parameter. In SI units the magnetic susceptibility is a dimensionless proportional-ity constant that indicates the degree of magnetization induced in a material in response to an applied magnetic field, and is defined by:

$$M = \chi H$$

where M is the magnetisation of the material (the mag-netic dipole moment per unit volume), measured in amperes per meter, H is the magnetic field strength, also measured in amperes per meter, and $\chi$ is the dimensionless proportionality constant, the magnetic susceptibility. Strictly speaking, $\chi$ is only constant for paramagnetic or diamagnetic materials, however, in soft magnetic or superparamagnetic materials where the magnetic hysteresis effect is small, and for applied fields H that are much less than the field required to magnetically saturate the materials, the linear relation-ship M=$\chi$ H is a good approximation.

Magnetic susceptibility can be measured by a range of known methods including the Faraday balance, Gouy bal-ance, the magnetic resonance method, and the inductive method with SQUID magnetometer. Magnetic susceptibility can also be calculated using computer-based finite element magnetic modelling packages such as ANSYS Maxwell (ANSYS Inc., Canonsburg, PA), by modelling the marker in a homogenous field and measuring the distortions caused by the marker which correspond to the magnetic susceptibility. See for example the method described in: "Magnetic Sus-ceptibility Modelling Using ANSYS", K. Bartusek et al., Progress In Electromagnetics Research Symposium Pro-ceedings, Marrakesh, Morocco, Mar. 20-23, 2011.

For a given material, a magnetic mass susceptibility can be defined which is the induced magnetic response per unit mass of the material. Magnetic mass susceptibility, $\chi_p$=k/p where p is the density of the material and $\chi_p$ has units of m³/kg. This is a normalized susceptibility and allows the relative susceptibilities of different materials to be com-pared. For example, the magnetic mass susceptibility of 316 stainless steel, a standard material for biopsy markers, has a range of approximately is approximately $3.80 \times 10^{-7}$ to $1.27 \times 10^{-6}$, a permanent Neodymium magnet has a value approxi-mately of $6.67 \times 10^{-6}$, Super Paramagnetic Iron Oxide (SPIO) based markers have a value of approximately $2.5 \times 10^{-5}$-$1.0 \times 10^{-3}$ depending on the density of particles in a matrix, while NiZn-ferrites have a range of approximately $3 \times 10^{-3}$ to $1.22 \times 10^{-1}$. Therefore, the NiZn-ferrites require less material to be detected than SPIO which in turn require less material than permanent Neodymium magnetic material or 316 stainless steel.

For a magnetically soft marker of volume V, subject to a field H in the linear susceptibility region, the total induced moment on the marker will be m=M V=$\chi$ V H. This moment will give rise to its own magnetic field $H_{marker}$, which at a distance removed from the marker may be approximated as that due to an equivalent point dipole moment, namely:

$$H_{marker}(r) \cong \frac{1}{4\pi}\left(\frac{3r(m \cdot r)}{r^5} - \frac{m}{r^3}\right)$$

where r is the unit vector. It is this induced field, $H_{marker}$, that is measurable and which makes the magnetic marker local-izable.

However, there are other factors that may affect the case with which a given marker may be located—or in other words, affect the strength of the induced field, $H_{marker}$, at a given r. One of these is known as 'demagnetization'. This is a phenomenon that occurs in objects of finite size, where the induced field due to the magnetization in one part of the body acts to demagnetize another part of the same body. The effect is very complex to predict in other than the most simple geometries, and is therefore most often described, as here, for the special case of the object being an ellipsoid of revolution (e.g. a sphere, cylinder or disk). In such a case, the induced magnetization within the object is uniform, and the local magnetic field is commonly written:

$$H_{local} = H - H_{demag} = H - NM$$

where $H_{demag}$ is the 'demagnetisation field' and N is the 'demagnetisation factor', although more accurately $H_{demag}$ should be defined along the x,y,z principal axes of the ellipsoid, as:

$$H^x_{demag} = N_x M_x, \; H^y_{demag} = N_y M_y, \text{ and } H^z_{demag} = N_z M_z.$$

In SI units $N_x+N_y+N_z=1$. For the case of a sphere, $N_x=N_y=N_z=\frac{1}{3}$. For the case of a long z-axis cylinder, $N_x=N_y=\frac{1}{2}$ and $N_z=0$. For the case of a thin xy-plane disk, $N_x=N_y=0$ and $N_z=1$. In the case of a marker made from a given single material of a given mass, the shape of that marker will affect the ease with which it may be localized.

For example: if the marker is made into a sphere, it will experience $H_{local}=H-\frac{1}{3}$ M, irrespective of the orientation of the marker to the applied field. The induced moment will therefore be:

$$m = \chi V H_{local} = \chi V H - 1/3\chi m, \text{ or } m = \chi V H/(1 + 1/3\chi)$$

The induced field, $H_{marker}$, will therefore also be reduced by a factor of $(1+\frac{1}{3}\chi)$ at any given r, but this reduction will be present irrespective of the orientation of the marker to the magnetizing field H.

In contrast: if the marker were made into a cylinder, then if H was directed perpendicular to the long axis of the cylinder, then $H_{marker}$ would be reduced by a factor of $(1+\frac{1}{2}\chi)$, whereas if H was directed along the long axis, $H_{marker}$ would not be reduced at all. In this case the ratio $\xi=(1+\frac{1}{2}\chi)/1$ represents the anisotropic localization signal that the cylinder would present to any method dependent on the magnitude of $H_{marker}$ for its signal strength.

In the case of a cylinder of finite length, this ratio may be approximated as:

$$\xi = \frac{1 + N_\perp \chi}{1 + N_\parallel \chi}$$

where $N_\perp=N_x=N_y$, and $N_\parallel=N_z=1-2 N_\perp$. For example, in the case of the ferritic stainless steel samples listed in Table 2, for which $\chi$ is approximately 140, the measured $\xi$ ratio of 10.3:1 for a cylinder of aspect ratio 7:1 corresponds to an $N_\perp$ of approximately 0.48; while the same material in a cylinder of aspect ratio 3.7:1 exhibited an anisotropy ratio $\xi$ of approximately 4.7:1, corresponding to an $N_\perp$ of approximately 0.44.

Thus, for a magnetic marker, the magnetic response depends partly on the mass susceptibility of its constituent material or materials, and partly on the shape of the marker, and for a given shape, the response can change with orientation of the marker. The anisotropy of the magnetic response can be calculated by using demagnetization factors as outlined above. However, as demagnetization factors are very difficult to calculate for real shapes, a more practical approach is needed to define the anisotropy of the response. The change in magnetic response with orientation for a given marker can be thought of as a change in the 'effective susceptibility' of the marker. The underlying susceptibility of the marker material does not change, but the change in magnetic response due to the combination of material, shape and orientation can be defined as if the susceptibility were varying.

Thus, for any given marker, a ratio can be defined of the maximum (effective) magnetic susceptibility to the minimum (effective) magnetic susceptibility. This ratio can be referred to as the anisotropy of the magnetic susceptibility and gives an indication of the uniformity of the magnetic susceptibility response along different axes of the marker or from different directions.

$$\text{Anisotropy of magnetic susceptibility} = \frac{\text{Maximum magnetic susceptibility}}{\text{Minimum magnetic susceptibility}}$$

As magnetic susceptibility is dimensionless, the anisotropy of magnetic susceptibility, being a ratio of two dimensionless quantities, is also dimensionless. If the anisotropy is 1, the susceptibility is the same from any direction. If the anisotropy is high, the susceptibility is very non-uniform with respect to the orientation of the marker.

The concept of anisotropy of magnetic susceptibility is described in the art and can be measured by a number of methods. For example, two types of directional susceptibility meter are described in A. K. Dubey, "*Understanding an Orogenic Belt*", Springer Geology: An equal-impedance bridge where the specimen can be inserted into a coil; and a balanced-transformer system where the specimen is placed inside a ferrite ring. A further method called a three dimensional magnetic anisotropic susceptibility meter is described in U.S. Pat. No. 3,492,566. In each case, a consistent magnetic field is applied to the sample, and the variation in the induced magnetic response is measured as the sample orientation is varied. A further such method is shown in FIG. 2(C) in which a susceptometry probe is used to measure the induced magnetic response. Using a magnetic susceptometer system, similar to that described in US Publication No. 2011/0133730, markers produced from various materials and in various forms had their maximum and minimum signals measured at a fixed distance. Results are shown in FIGS. 2(E)-2(J).

Measuring the anisotropy of magnetic susceptibility using a magnetic susceptibility probe or meter is the ideal approach to defining the uniformity of the magnetic response of a marker. However, there are alternative approaches to determining the level of anisotropy of magnetic susceptibility. For example, the projected area of the marker in any direction can be measured and maximum and minimum projected areas determined. For a given volume of marker material, a lower projected area indicates a greater focusing effect of the field and visa versa. As the focusing effect is inversely proportional to the projected area, the uniformity of response can thus be defined by the ratio of the minimum projected area to the maximum projected area of the marker out of all the available viewpoints or directions. This is the projected area anisotropy ratio of the magnetic marker, and provides a useful approximation to the anisotropy of magnetic susceptibility. A spherical marker would have a ratio of the minimum projected area to the maximum projected area=1. A rod shaped marker of diameter, d=0.75 and length, l=7.5 would have a ratio of $d \times l/(pi \times d^2/4)=12.7$.

It can also be seen that this ratio of projected areas is approximately equal to the shape factor of the marker, which is defined as the ratio of the largest dimension of the marker to its smallest dimension and this too can be used as an approximation to the anisotropy of magnetic susceptibility. Both these geometric methods do not account for variations in the magnetic properties within the marker.

Where the term 'anisotropy of magnetic susceptibility' or magnetic anisotropy is used throughout, the term 'projected area anisotropy' or 'ratio of largest to smallest dimension' are understood as alternative interchangeable measures of the uniformity of the magnetic response.

The anisotropy of magnetic susceptibility can be determined for the marker both before deployment when in the delivery device and after deployment. Where the marker configuration changes, the anisotropy of magnetic susceptibility may have a different value before and after deployment.

From a practical perspective, during surgery to detect the marker using a magnetic probe as described in WO2014/013235, high anisotropy is undesirable: the magnetic signal at a constant distance will vary depending on the orientation of the marker relative to the probe and make the marker appear to be closer when approaching from some orientations and further away from others. Minimising the anisotropy for the implanted marker improves the surgeons' ability to localise the marker by making it more intuitive and increases the surgeons' ability to remove a safe margin of tissue around a lesion. An anisotropy ratio of 1 is the ideal, giving a uniform response from any direction. However, in practice this is challenging to achieve within the geometric constraints of delivery through a small needle as outlined herein. An anisotropy ratio of less than 7 (i.e. between 1 and 7), preferably less than 5 and more preferably less than 3 is desirable. Because the magnetic response reduces with distance exponentially, an anisotropy ratio of less than 2 is close enough to the ideal for practical use.

An ideal magnetic marker becomes magnetized in the presence of a magnetic field and exhibits no permanent magnetic remanence (retained magnetisation) when the field is removed, or in other words, an ideal marker is magnetically soft, i.e. formed from magnetically soft material or behaving as if it is magnetically soft. Magnetically soft is here defined as having a magnetic coercivity, Hc, of less than or equal to 1000 Oe, or preferably less than or equal to 100 Oe or more preferably less than or equal to 50 Oe is desired in various embodiments. During detection, the marker is magnetised and follows the dotted curve shown in FIG. 1, returning via the solid line when the magnetic field is removed or reversed. When an alternating magnetic field is applied, the magnetizing drive field (H) pushes the material along the solid magnetisation curve around the loop once for each cycle. The induced field in the material (termed the magnetization, M) is detected by the susceptometer probe, for example the probe of US Publication No. 2011/0133730. Ideal marker materials are soft and have a magnetization curve similar to that in FIG. 1A.

It should be noted that permanent magnets are magnetically hard, having both a high magnetic remanence and a high magnetic coercivity (FIG. 1(B)). They are generally unsuitable for use as a magnetic marker in this application because they can attract or be attracted by other ferromagnetic objects such as surgical tools and because they typically have very low magnetic susceptibility.

The amount of material required to be implanted to make a magnetic marker detectable depends upon the magnetic susceptibility ($\chi_v$) of the material, more specifically the magnetic mass susceptibility ($\chi_p = \chi_v / p$), which can be expressed as:

$$\chi_\rho = (\mu_r - 1)/\rho$$

where $\mu_r$ is the relative magnetic permeability and p is the material density.

The material used in the magnetic marker should have a relative permeability greater than 100, and preferably greater than 500. When specialist magnetic materials such as high purity iron or amorphous materials such as metallic glasses are used, relative permeability is greater than 1000 and preferably greater than 5000. The marker should have a high magnetic mass susceptibility, $\chi_p$. For conventional magnetic materials such as irons, steels and ferrites, $\chi_p$ should be greater than or equal to 0.05 m³ kg⁻¹, preferably greater than or equal to 0.1 m³ kg⁻¹ and more preferably greater than or equal to 1 m³ kg⁻¹. The use of specialist magnetic materials such as high purity iron or amorphous materials such as metallic glasses allows even higher magnetic mass susceptibilities, and $\chi_p$ is preferably greater than 5 m³ kg⁻¹ and more preferably greater than 10 m³ kg⁻¹.

If material magnetic mass susceptibility is high enough, a spherical marker, which is capable of being deployed from the conventional needle described, would be capable of being magnetically localised and provide a perfectly isotropic signal. Table 1 shows mass susceptibilities for a number of magnetic materials.

TABLE 1

| Material | Magnetic Mass Susceptibility, $\chi_\rho$ (m³kg⁻¹) |
| --- | --- |
| Metglas | 127 |
| Iron (99.95% pure Fe annealed in H) | 25.3 |
| Nanoperm | 10.9 |
| Mu-metal | 2.29-5.72 |
| Cobalt-Iron (high permeability) | 2.22 |
| Permalloy | 0.917 |
| Iron (99.8% pure) | 0.633 |
| Electrical steel | 0.506 |
| Ferrite (manganese zinc) | 0.128 to 0.300 |
| Ferritic stainless steel (annealed) | 0.128 to 0.231 |
| Ferrite (nickel zinc) | 0.003 to 0.128 |
| Martensitic stainless steel (annealed) | 0.096 to 0.122 |
| Nickel | 0.0111 to 0.0673 |
| Carbon Steel | 0.0127 |
| Martensitic stainless steel (hardened) | 0.005 to 0.0121 |
| 301 (55% cold worked) | 0.00165 |
| 304 (80% cold worked) | 0.000380 |
| Neodymium permanent magnet | 0.00000667 |
| Samarium Cobalt permanent magnet | 0.00000602 |
| 316 (81% cold worked) | 0.00000127 |
| 304 (annealed) | 0.000000506 |

TABLE 1-continued

| Material | Magnetic Mass Susceptibility, $\chi_\rho$ (m³kg⁻¹) |
| --- | --- |
| 316 (annealed) | 0.000000380 |
| Nitinol | 0.000000297 |
| Platinum | 0.0000000124 |
| Titanium | 0.0000000111 |
| PET | 0.000000000714 |
| Gold | -0.000000000104 |
| PTFE | -0.00000000182 |
| Silicone | -0.00000000200 |
| Water | -0.00000000800 |
| Carbon graphite | -0.0000000190 |

Various material magnetic mass susceptibilities
Note:
negative values denote diamagnetic material.

The detection and localization of these magnetic markers can be performed with a sensitive magnetometer (or susceptometer) which generates an alternating magnetic field, to excite the marker magnetically, and detects the magnetic field signature generated by the marker, as disclosed in US Publication No. 2011/0133730. The marker could also be detected by other techniques such as MRI, magnetic particle imaging, eddy current measurement, hall effect, or magnetotomography.

In one aspect of the invention, the marker comprises superparamagnetic particles. Superparamagnetic particles typically contain an iron oxide (magnetite and/or maghaemite) core surrounded by a biocompatible coating such as dextran, carboxydextran, other sugars, albumin, PEG, or biocompatible polymers. To exhibit superparamagnetic behaviour, the particles' magnetic cores need to be below a critical diameter, typically in the range 3-25 nm depending on the material and structure.

Iron oxide is the preferred material for the superparamagnetic core because of its low toxicity, but there are other materials which could form a superparamagnetic core. The material of the core should be one that is capable of being magnetically ordered. It may be a metal, such as cobalt, iron, or nickel; a metal alloy, rare earth and transition metal alloy, M-type or spinel ferrite containing aluminium, barium, bismuth, cerium, chromium, cobalt, copper, dysprosium, erbium, europium, gadolinium, holmium, iron, lanthanum, lutetium, manganese, molybdenum, neodymium, nickel, niobium, palladium, platinum, praseodymium, promethium, samarium, strontium, terbium, thulium, titanium, vanadium, ytterbium, and yttrium or a mixture thereof.

The core can also be formed by oxidising a combination of an iron (II) salt and another metal salt. The metal salts which are beneficial include salts of aluminium, barium, bismuth, cerium, chromium, cobalt, copper, dysprosium, erbium, europium, gadolinium, holmium, iron, lanthanum, lutetium, manganese, molybdenum, neodymium, nickel, niobium, palladium, platinum, praseodymium, promethium, samarium, strontium, terbium, thulium, titanium, vanadium, ytterbium, and yttrium.

In another aspect of the invention, the marker comprises a solid, magnetically soft material to provide a significantly increased magnetic response when being localised with a magnetic susceptometry probe. Markers produced from magnetically soft materials can include various paramagnetic, ferromagnetic and ferrimagnetic materials such as iron, nickel, cobalt and their alloys, electrical iron (including FM, consumet electrical iron), silicon-irons (including "A", "A-FM", "B", "B-FM", "C" variants) iron-phosphorous, nickel-iron (e.g. HyRa alloys, HyMu alloys, Hipernom, Parmalloy, Superalloy, Mu-metal), Heusler alloys, Fernico alloys (Iron-Nickel-Cobalt based alloys), Cunife alloys (Copper-Nickel-Iron based alloys), Alcomax alloys (Iron-Nickel-Aluminium-Cobalt-Copper based alloys) various stainless steels from the 300 series (e.g. 302, 304, 316), 400 series (e.g. 410, 416, 420, 430, 440, 446, 470) as well as specialist stainless steel alloys (e.g. chrome-iron alloys such as Chrome-Core® series (Carpenter Technology Corp, Wyomissing PA), martensitic stainless steels), ferrites such as MnZn-ferrites, NiZn-ferrites, MgZn-ferrites, Ba-ferrites, MnMgZn-ferrites, and MgZnCu-ferrites.

In a preferred aspect of the invention, the marker comprises a metallic glass with a very high magnetic mass susceptibility to provide a significantly improved magnetic response. Metallic glasses are also known as amorphous metal or bulk metallic glass and include Fe or Co based material such as those produced by Metglas Inc. (Conway, SC) or Neomax Materials Co. Ltd (Osaka, Japan); and magnetic carbon allotropes (e.g. fullerenes, highly oriented pyrolitic graphite, carbon nanofoams, nano-porous carbon). Examples of metallic glasses include but are not limited to: FINEMET, NANOPERM, HITPERM (all Hitachi Metals, Tokyo, Japan), METGLAS #2605, METGLAS #2826, METGLAS #2615, METGLAS #2714A, METGLAS #2605.

In order to ensure biocompatibility, these materials may be coated or contained within a biocompatible or inert material for example Bioglass, diamond-like-carbon (DLC), gold, hydroxyapatite, Iron, magnesium, nitinol, parylene, phosphorylcholine (PC) polymer, Poly-butyl methacrylate (PMBA) and polyethylenevinyl acetate (PEVA), polyethyl- DL-Lactide/Glycolide, DL-Lactide/Caprolactone, Glycolide/Caprolactone, L-lactide/Glycolide/Caprolactone, DL-Lactide/Glycolide/Caprolactone, Poly(dioxinone co-trim ethylene carbonate-co-glycolide)Glykomer 631 (marketed as Biosyn®); or copolymers of these with PDS, hydrogels (from one or more monomers of Hydroxyethyl methacrylate, Hydroxyethoxyethyl methacrylate, Hydroxydiethoxyethyl methacrylate, Methoxyethyl methacrylate, Methoxyethoxyethyl methacrylate, Methoxydiethoxyethyl methacrylate, Ethylene glycol dimethacrylate, N-vinyl-2-pyrrolidone, N-isopropyl AAm, Vinyl acetate, Acrylic acid, MAA, N-(2-hydroxypropyl) methacrylamide, Ethylene glycol, PEG acrylate, PEG methacrylate, PEG diacrylate, PEG dimethacrylate).

In one aspect of the invention the implanted marker is made from a single magnetically soft material and the marker is shaped to reduce the anisotropy of the magnetic response. This anisotropy is defined as the ratio of the maximum magnetic response to the minimum magnetic response. The anisotropy arises in shapes with a long thin aspect ratio because magnetically soft materials focus any magnetic field lines running through them. The focusing effect depends on the amount of material in the direction of the field lines. Thus, a long thin shape when its long axis is aligned with the field focuses many more field lines through the material than when its long axis is perpendicular to the field lines. The result is that the magnetic response measured by a susceptometer is much larger in the direction of the long axis than in the direction of the short axis.

Table 2 shows anisotropy ratios for a number of cylinders of magnetic material of various sizes.

TABLE 2

| Marker | Dimensional ratio length:diameter | Volume (mm³) | Signal Max | Signal Min | Anisotropy Ratio |
|---|---|---|---|---|---|
| Ferritic stainless steel | 3.7 | 2.1 | 3885 | 828 | 4.7 |
| Ferritic stainless steel | 7 | 4.7 | 1518 | 148 | 10.3 |
| Martensitic stainless steel | 7.4 | 3.1 | 1135 | 147 | 7.7 |
| Fe (99.99%) ø1.0 mm | 4 | 3.1 | 860 | 216 | 4.0 |
| Fe (99.95%) ø0.5 mm | 12 | 1.2 | 790 | 74 | 10.7 |
| Fe (99.5%) ø1.0 mm | 5 | 3.9 | 2535 | 321 | 7.9 |
| MnZn-Ferrite (ø1.0 mm) | 3.5 | 5.9 | 981 | 166 | 5.9 |
| Mu Metal multistrand (ø0.6 mm) | 8.3 | 1.4 | 1118 | 128 | 8.7 |

Ratios of anisotropy of magnetic susceptibility for cylinders of various sizes and materials at a constant distance.

ene, PET, polytetraflouroethyleene (PTFE), PEBAX, PEEK, PEKK, platinum, silicone, titanium and the like.

Further a shaped material such as a spring steel or shape memory materials alloys such as Nitinol, and shape memory polymers such as PEO-PET coblock polymers and PEEK could also provide additional function of forming a specific shape on deployment if surrounding or surrounded by a magnetically soft material.

Figure 18:
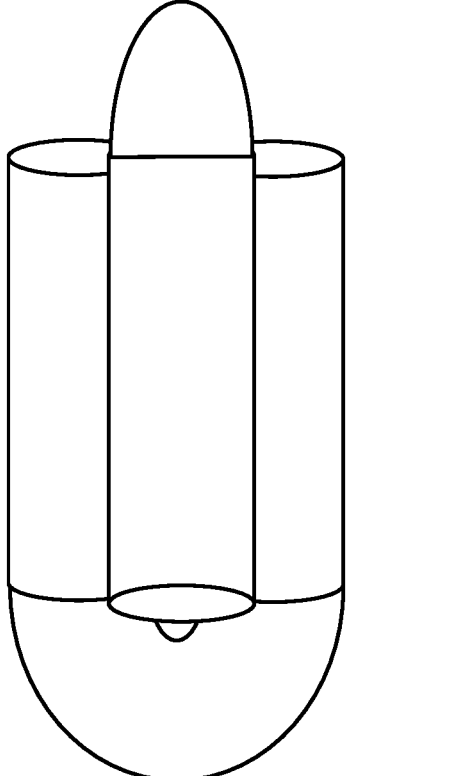
FIG. 18 is a diagram of an embodiment of two interlocking U shaped markers.

The magnetic material could further be held within a biocompatible matrix, such as collagen, gelatin and other cellulose base materials, Polyvinyl alcohol (PVA), Polyglyconate, polyester based materials (formed by homopolymerization or copolymerization of one or more of these monomers: glycolide, L-lactide and its isomers, &-caprolactone, p-dioxanone and trimethylene carbonate (TMC). These may include homopolymers such as: Poly(L-lactide) Poly(DL-lactide), Poly(TMC), Polycaprolactone (PCL), Polyglycolide (PGA), Poly(glycolide-L-lactide) (PGL), or Poly(p-dioxanone) (PDS); or co-polymers such as: L-Lactide/DL-Lactide, L-lactide/Glycolide, L-lactide/Caprolactone, By altering the shape to influence the focusing effect, the anisotropy can be altered. For example, by creating a bend in the marker the anisotropy ratio for a given pre-deployment dimensional ratio can be reduced significantly (FIGS. 2(E)-2(J)). A 130° included angle surprisingly reduces the ratio from 6.7 to 4.5 and a U bend reduces it further to 2.1. In another example, a 90° bend reduces the ratio from 10.7 to 2.6, and a 60° included angle reduces the ratio further to 1.28. Referring again to Table 2, using a magnetic susceptometer system, similar to that described in US Publication No. 2011/0133730, markers produced from various materials and in various forms had their maximum and minimum signals measured at a fixed distance. The graph shows that there is an optimum angle for a uniform signal when the angle is between 0° and 90°, and more preferably between 0° and 45°. FIG. 18 shows how the signal varies with the angle of sensing relative to the marker's main axis for markers with different included angles. FIGS. 2(E)-2 (J) show an anisotropy ratio for various shapes and sizes of magnetic markers at a constant distance.

Figure 2A:
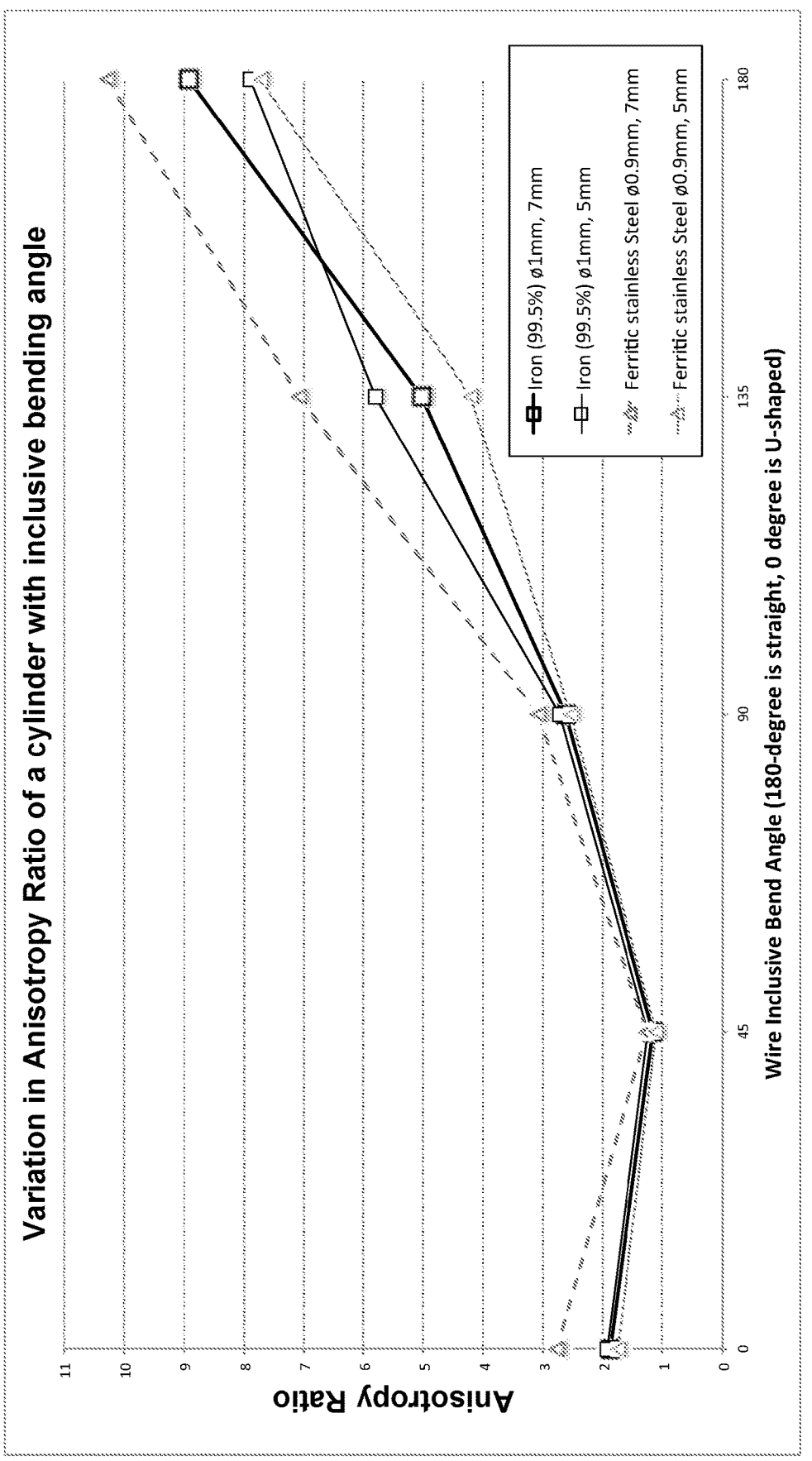
FIG. 2(A) is a graph of the influence of marker bend angle on anisotropy of susceptibility of a marker.
Figure 2B:
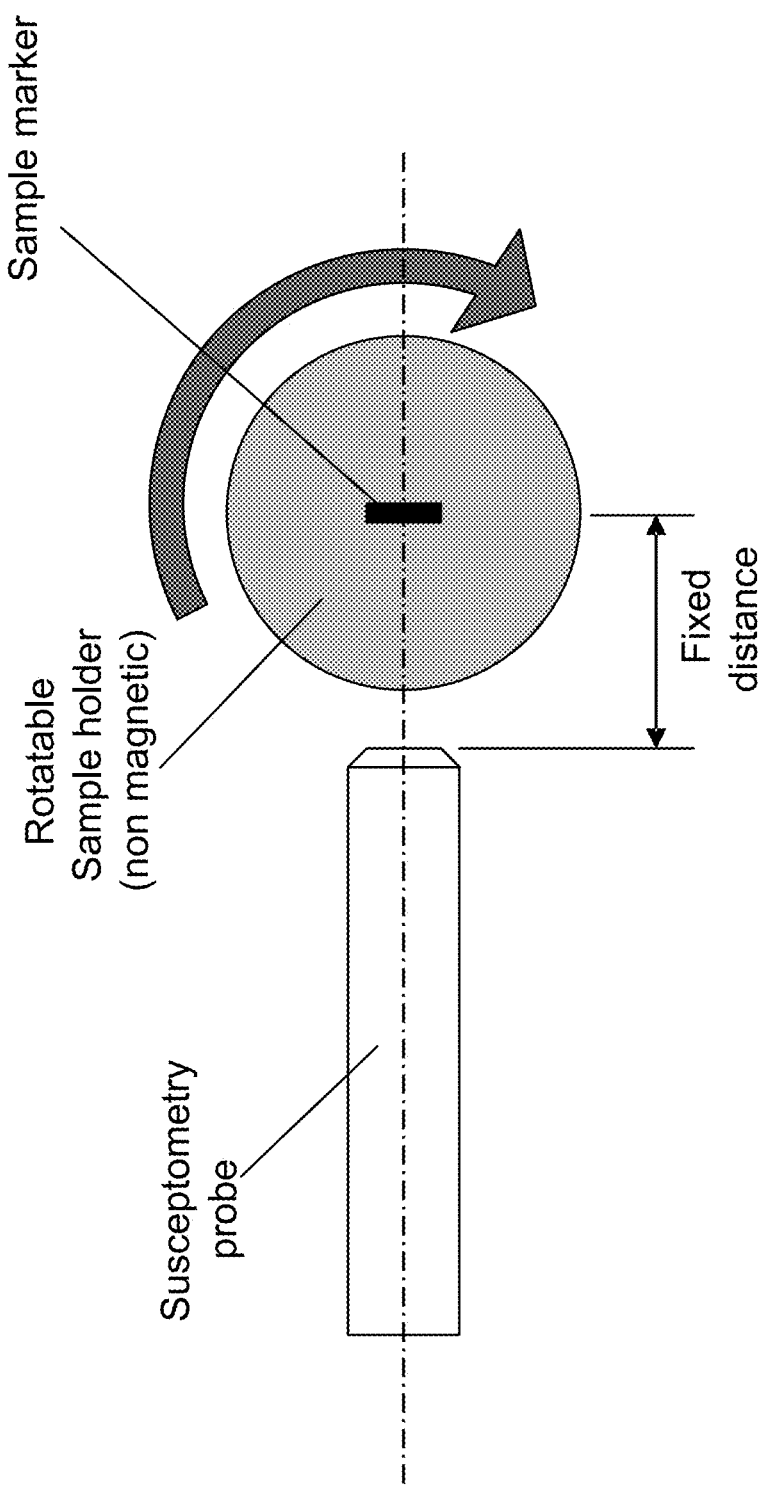
FIG. 2(B) is a diagram of an embodiment of a test arrangement for measuring magnetic anisotropy of a marker.
Figure 2C:
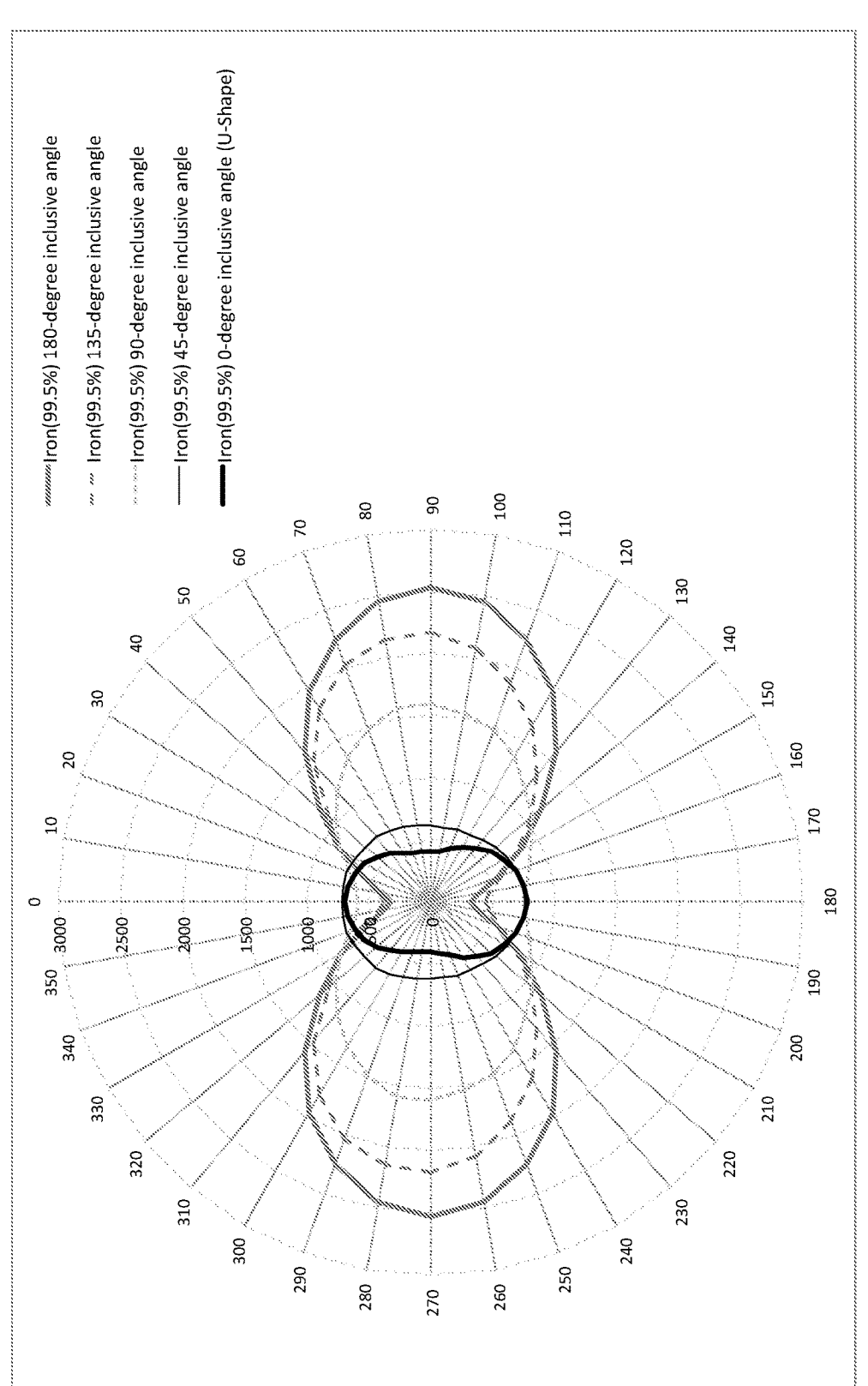
FIG. 2(C) is a signal at a constant distance from 5 mm Iron (99.5%) markers with various inclusive angles, where 180-degrees is a straight cylinder and 0-degrees is U-shaped.
Figure 2D:
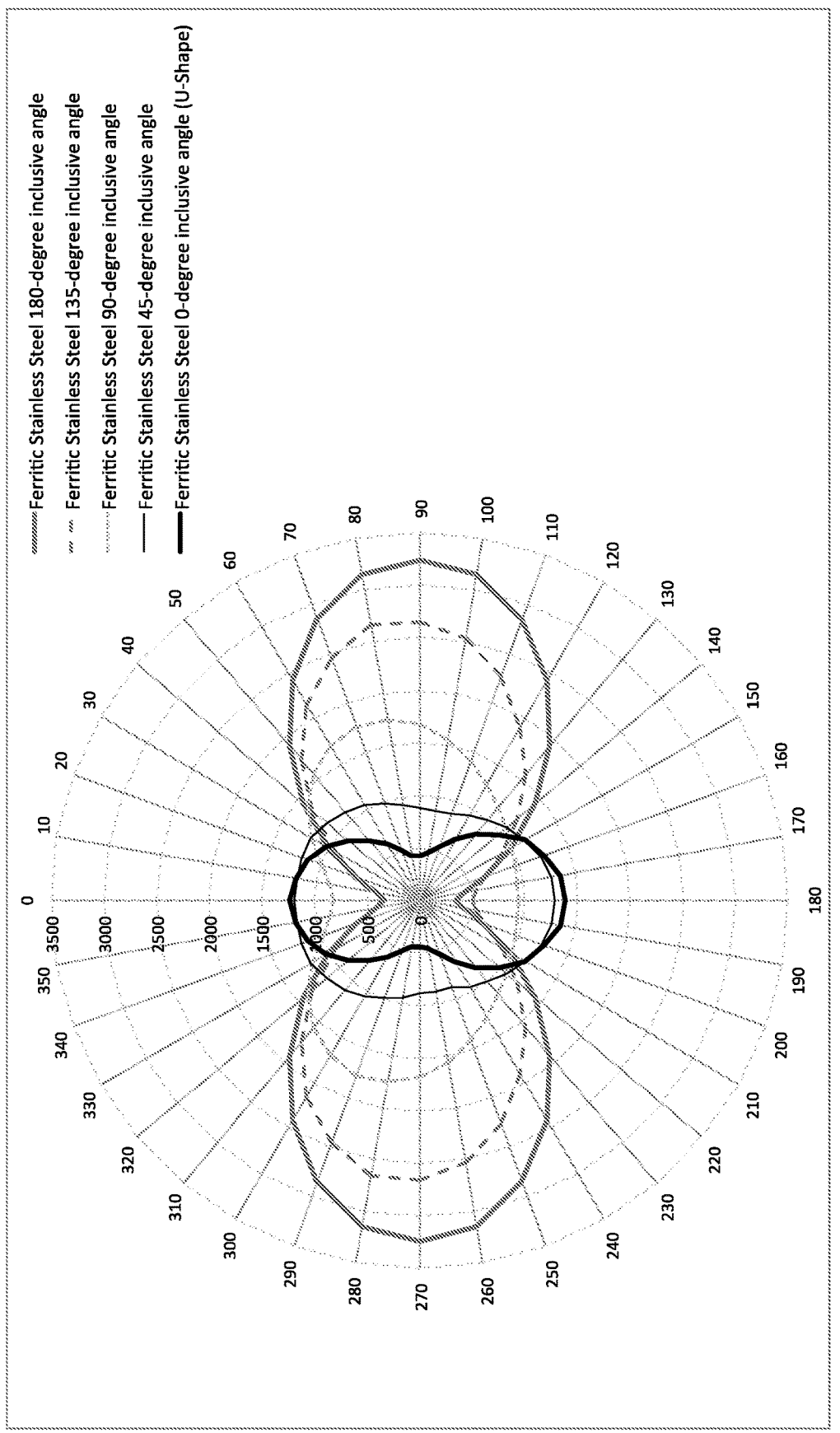
FIG. 2(D) is a graph of a signal at a constant distance from 7 mm multi-stand stainless steel markers with various inclusive angles, where 180-degrees is a straight cylinder and 0-degrees is U-shaped.

FIG. 2(A) is a graph of the relative change in anisotropy ratio as the included angle of a bend in the marker is reduced. The measurements were taken using the test arrangement in FIG. 2(B). The graph (FIG. 2A) shows that there is an optimum angle for a uniform signal when the angle is between 0° and 90°, and more preferably between 0° and 45°. FIG. 2(C) is a graph that shows how the signal varies with the angle of sensing relative to the marker's main axis for iron markers with different included angles. FIG. 2(D) is a graph that shows how the signal varies with the angle of sensing relative to the marker's main axis for iron markers with different included angles.

In some cases, it may be advantageous for the marker to assume the shape only after it has been deployed so that it can be packed more efficiently into the deployment needle prior to deployment. An elastic material or a section of elastic material may be used to facilitate this.

Figure 3A:
FIG. 3(A) is a diagram of an embodiment of the invention in the form of a "lozenge" or a "bead"
Figure 3B:
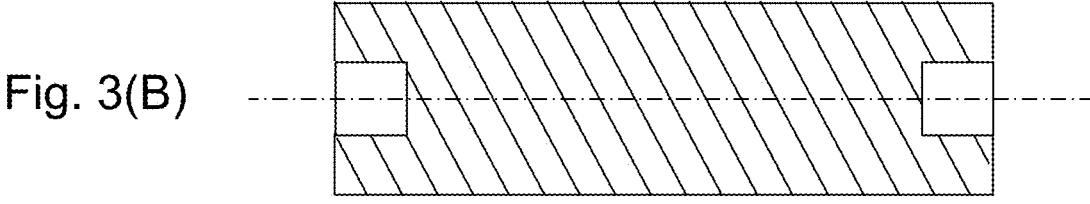
FIGS. 3(B) and (C) are cross-sections of magnetic beads with shaped ends.
Figure 3C:
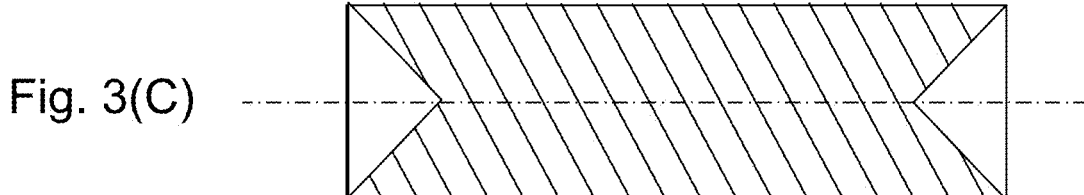
Figures 4A, 4B, 4C, 4D:
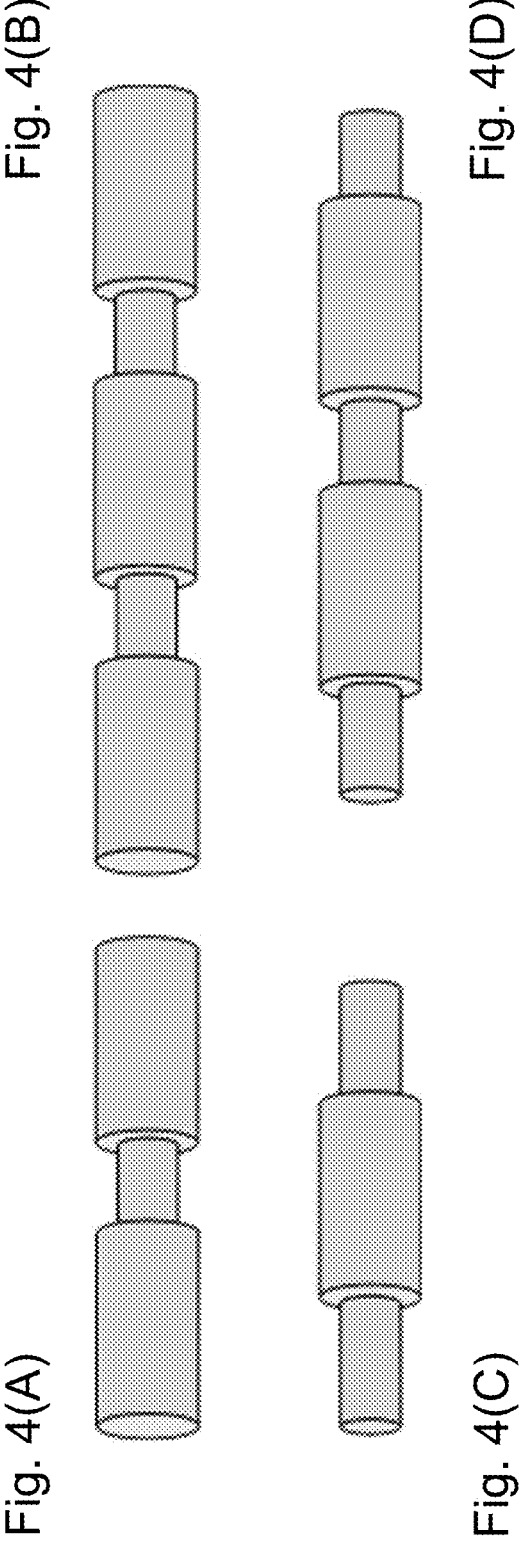
FIGS. 4(A)-(D) are diagrams of embodiments of the invention in the form of "dumbbell" shapes.
Figures 8A, 8B, 8C, 8D, 8E, 8F, 8G:
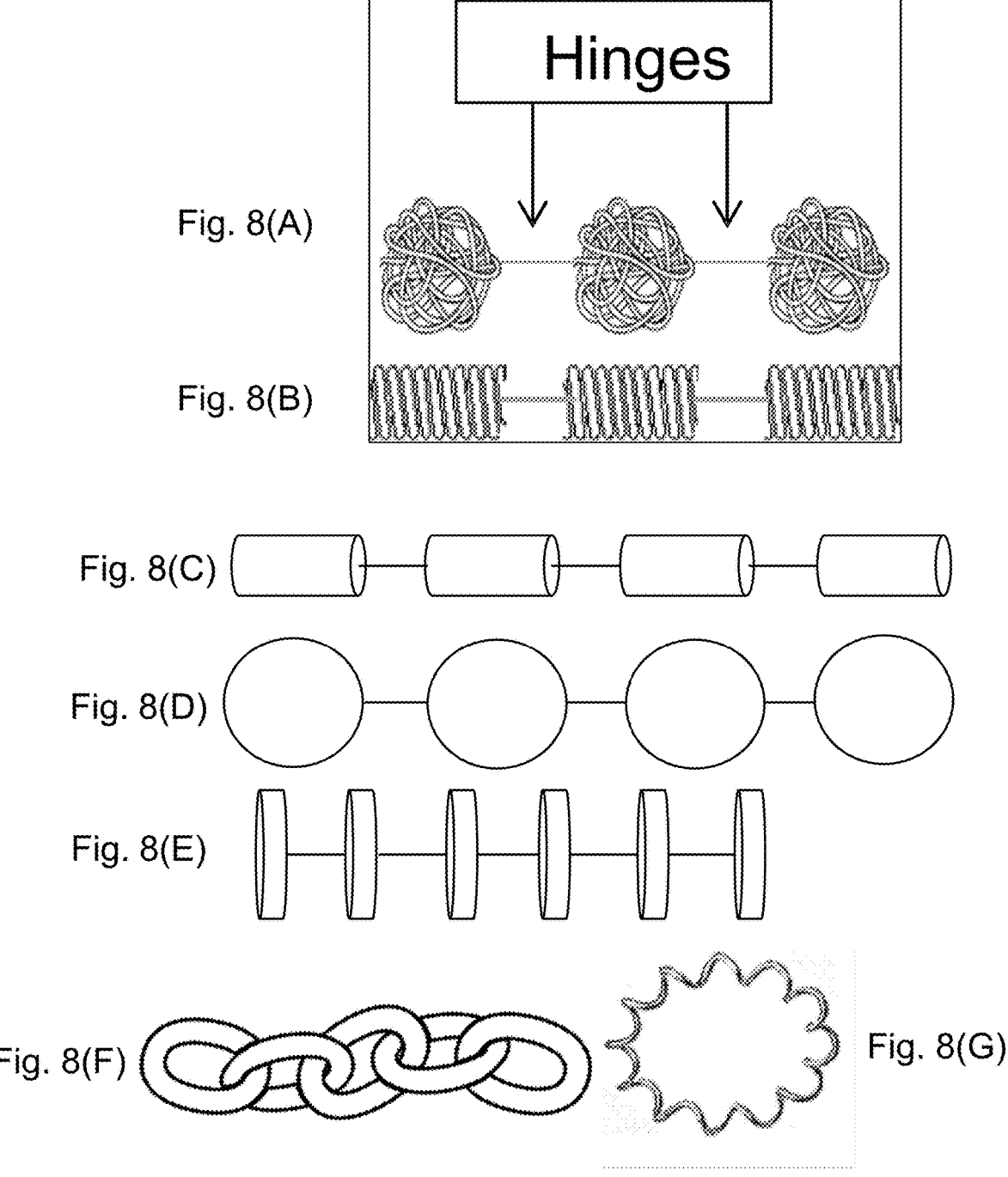
FIGS. 8(A)-(G) are diagrams of embodiments of the invention with hinged linkages.

Such shapes include, but are not limited to the following:

"lozenge" or "bead" shapes (FIG. 3(A)), that reduce the anisotropy by providing more magnetic material in the transverse axis (perpendicular to the long axis of the bead). Such markers may include shaped ends comprising narrower sections that focus the field in a direction away from the main axis (FIGS. 3(B) and (C)). For example, a finite element model of the marker of FIG. 3(C) and a probe of the type described in US Publication No. 2011/0133730 with the marker at a distance of 20 mm from the probe end gave an anisotropy ratio of magnetic susceptibility of 2.5;

"dumbbell-type" designs as shown in FIGS. 4(A)-(D), are constructed from segments of the same material. This design similarly provides more magnetic material along the transverse axis. In various embodiments, the markers being about 5-10 mm in length, and are useful in reducing the opposing eddy currents. For example, a finite element model of the marker of FIG. 4(E) and a probe of the type described in US Publication No. 2011/0133730 with the marker at a distance of 20 mm from the probe end gave an anisotropy ratio of magnetic susceptibility of 2.6;

cable or multi-wire strands as shown in FIGS. 5(A) and (B) and may be twisted. A number of stranding forms are illustrated, but other stranding forms such as 1×4, 1×5 etc. with 3, 4, 5, 6, 7 or more strands are equally viable; using strands reduces the opposing eddy current loss and having multiple facets provides superior ultrasound response. The wires could also be hollow as illustrated or include void areas between the strands;

bent wires or tubes including acute and obtuse angles, U shapes, X shapes (FIGS. 2(E)-2(J));

a single length of cylindrical marker divided into two or more small pieces of a similar size gives an improved anisotropy ratio of less than 5;

a cylindrical marker with a larger diameter central section and smaller diameter outer sections also gives an improved anisotropy ratio;

markers composed of two interlocked U shaped elements (FIG. 18).

In one aspect of the invention, the implanted marker is made primarily from a magnetically soft material and the marker has a long thin aspect ratio prior to deployment but changes configuration after deployment to a shape with a low anisotropy of the magnetic susceptibility. Prior to deployment, the marker may have a length to diameter ratio or shape factor of greater than 5, and a ratio of magnetic anisotropy of susceptibility of greater than 5 or even greater than 7 or 9, such values resulting from the extended length of the marker prior to deployment and being beneficial to increase the volume of marker contained in the needle so as to maximize the magnetic response once deployed. After deployment, the ratio of magnetic anisotropy of susceptibility is less than 5 and preferably less than 3, and ideally 2 or less to provide a more uniform magnetic response.

In one aspect, the marker is elastically deformable or resiliently deformable such that it elastically or resiliently changes in shape and size from a packed or pre-deployment shape within the needle or deployment device with an associated shape factor, to a post-deployment shape and shape factor. The elasticity or resilience may, for example, derive from the use of an elastic or resilient material or from an elastic, resilient or deployable structure or combinations thereof. Preferably, the magnetic marker is elastically or resiliently deformable between a packed configuration having a higher anisotropy of magnetic susceptibility, and a deployed/unpacked configuration having a lower anisotropy of magnetic susceptibility. Alternatively, the magnetic marker is elastically or resiliently deformable between a packed configuration having a higher projected area anisotropy ratio, and a deployed/unpacked configuration having a lower projected area anisotropy ratio.

Preferably the deployed or delivered configuration of the marker has an anisotropy of magnetic susceptibility of less than 5, more preferably less than 3 and ideally less than 2 in order to give the most uniform detection signal; while prior to deployment within the delivery device, the marker in its packed configuration has an anisotropy of magnetic susceptibility of greater than 5 and more preferably greater than 7, in order to maximize the volume of material in the marker given the constrained diameter of the delivery device. By analogy, the marker in its packed configuration has a projected area anisotropy ratio of greater than 5 and more preferably greater than 7; but in a deployed/unpacked configuration has a projected area anisotropy ratio of less than 5, more preferably less than 3 and ideally less than 2. In order to achieve this configuration change, the marker requires a degree of resilience whereby one dimension (e.g., the diameter perpendicular to the main axis) of the marker changes by a factor of, at least, 1.5 times from its packed value to its deployed value. Preferably the deployed dimension is larger than the packed dimension by a factor of greater than 2 and more preferably greater than 3 in order to provide a shape factor (ratio of maximum dimension to minimum dimension) close to 1 or 2 on deployment, while still having sufficient material to be detected.

The magnetic marker in its packed configuration is packed within a delivery device prior to use. The delivery device needs to be able to deliver the marker through the skin to mark the tissue area of interest, for example a cancerous lesion. Suitable delivery devices include any needle- or cannula-based delivery system, typically comprising a needle and means to propel the marker through the end or out of the side of the needle such as a plunger or stylet. The needle is preferably 14 to 18 gauge. This means that the needle has an internal diameter generally of 0.8 mm to 1.5 mm but may possibly be as large as 1.8 mm for certain needle designs. Preferably it is between 1.0 and 1.5 mm in diameter. If a vacuum-assisted needle is used, the needle size is typically 11 gauge, with an internal diameter of 2.3 to 2.5 mm.

Markers that achieve the desired change in anisotropy of the magnetic susceptibility between their packed and unpacked configurations include, but are not limited to the following:

"ball of yarn" type forms (FIGS. 6(A) and (B)) that reduce the anisotropy by providing a substantially uniform amount of magnetic material in any given axis of the marker. The multiple facets provide also superior ultrasound response. A ball of yarn is preferably formed from a material with a large magnetic response such as a metallic glass or a magnetically soft material from the list above. The ball may be formed from a fine wire of diameter for example between 10 μm and 250 μm and length for example of between 5 mm and 150 mm, and bent into the shape of the ball. The marker may be elastically deformable or resiliently deformable. The marker is compressed to fit inside the deployment needle or delivery device, where, prior to delivery, it may be constrained to take a more cylindrical shape. On deployment the ball expands to close to its original size and takes a substantially spherical shape. FIGS. 2(E)-2(J) show that this marker can achieve an anisotropy ratio of close to the ideal of 1.

"Chinese-lantern" forms (FIG. 7). On deployment, this marker is arranged such that it resiliently reconfigures from a cylinder to a more compressed lantern configuration, thus increasing the uniformity of the magnetic response (reducing anisotropy) because the amount of material in the transverse axis is increased from that of a cylinder. The multiple facets also provide superior ultrasound response.

Markers comprising a plurality of magnetically soft elements joined with hinges as shown in FIG. 8(A)-(G) that deform into shape on deployment (either plastically, prestressed or through the action of a shape-memory in the material). The greater length of the marker in this embodiment is possible because the shape of the marker in the deployment needle is linear but folds to another configuration upon injection into a site. This reduces the anisotropy by providing a substantially uniform amount of magnetic material in any given axis of the marker.

Advantageously, the multiple facets also provide superior ultrasound response. It is desirable to have at least 3 elements to obtain a uniform response, and many more may be added, although for complexity the number is preferably less than 20 and more preferably less than 10. The hinged and other flexible or resiliently deformable forms may comprise a plurality of smaller magnetic units or components joined by non-magnetic flexible or resiliently deformable links such as plastic or shape memory materials. Combinations of these forms, e.g., bent wire made from multi-strand cable, are also included. As shown in FIGS. 2(E)-2(J), a marker of this kind with multiple ball elements and a pre-deployment geometric length: diameter ratio of 8 can have a post-deployment magnetic anisotropy of susceptibility of less than 2.

Markers comprising a plurality of elements joined with collapsible links between them such that on deployment the elements collapse together to form an amorphous region with a low ratio of magnetic anisotropy of susceptibility. The links can be formed from a string-like material such as suture or other polymer. Preferably, the magnetically soft elements are links in a chain that can collapse on itself after deployment.

Markers comprising a springy or resiliently deformable wire, or cylindrical shape prior to deployment that on deployment forms a structure or wireframe. Such structures may include a cylindrical coil, helix, conical coil, spherical coil, random 'ball of yarn', or a polyhedron such as a tetrahedron or part thereof.

Markers comprising a resiliently deformable looped or shaped coil spring that is compressed prior to deployment and expands upon deployment to a shape with a low ratio of magnetic anisotropy of susceptibility. For example, a coil spring shaped into a circle gives a surprisingly low ratio of magnetic anisotropy of susceptibility (FIGS. 2(E)-2(J)). Preferably, the ratio of the circle diameter to the spring coil diameter is less than 5 in order to maintain a more uniform magnetic response.

Markers comprising two or more elements connected by a link formed from an elastic or resiliently deformable or springy material such that the elements once deployed spring into a new configuration giving a low magnetic anisotropy of susceptibility. FIGS. 2(E)-2(J) illustrate one such embodiment comprising two short cylindrical elements formed of magnetically soft material joined by a spring filament. In the deployment needle, the two elements are constrained to be aligned axially joined by the filament. The filament is biased such that on deployment the two elements spring back across each other to approximate a tetrahedral shape with a low ratio of magnetic anisotropy of susceptibility of less than 2. The spring filament may be formed from a spring steel, shape memory material or other elastic or resiliently deformable material. Preferably, the length of the cylindrical elements is between 2 and 5 times their diameter to provide good uniformity of response combined with a compact shape. In a further embodiment of this concept, multiple elements on a springy material are deployed from the needle and the springy material is biased such that on deployment the elements are formed into a structure. Example structures may include a cylindrical coil, helix, conical coil, spherical coil, random 'ball of yarn', or a tetrahedron or part thereof. In these designs the length of the marker when in its packed configuration may be between 2 and 5 times their diameter but could be even greater e.g. up to 10 or more times the diameter depending on the degree of elasticity of the structure of material being used, thus allowing more magnetic material to be deployed to maximize the detectability of the marker.

Figure 9:
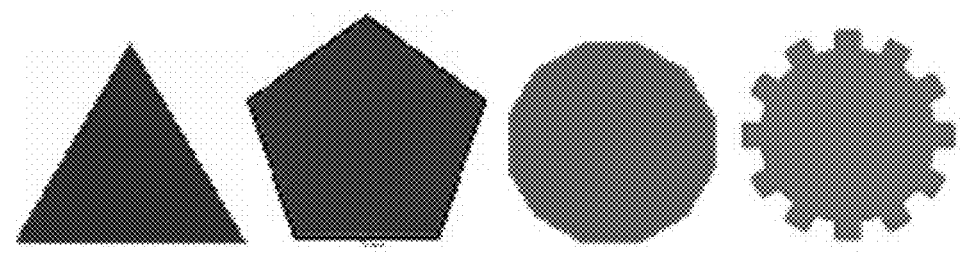
FIG. 9 is a collection of diagrams of cross-sections of embodiments of markers of the invention with increased numbers of faces.

A further benefit of the "ball of yarn" (FIG. 6) stranded or multi-facetted forms is superior visibility to such reflective imaging techniques as ultrasound, IR or ultra-wideband radar. These benefits can also be realised by revision of the external surface of the other forms mentioned, including the non-hinge sections of the hinged forms (FIG. 7) from cylindrical to facetted or grooved forms such as, but not limited to, triangular, pentagonal, dodecagon, cog-like cross sections (FIG. 9). A similar effect can be observed in ultrasound from sintered materials such as ferrites. Correct choice of soft material in any of the forms mentioned can provide visibility to X-ray imaging. Interlocked U's take similar space to U but with increased signal and reduced anisotropy (FIG. 18).

The above features can be combined to provide a marker with reduced anisotropy and improved imaging.

In a further aspect of the invention, the ratio of magnetic anisotropy of susceptibility of the implanted marker is modified by varying the magnetic properties of the magnetically soft material forming the marker along its length.

In another aspect of the invention, the reduction in magnetic anisotropy of susceptibility can be achieved through use of composite materials such as the formation of ferrite via sintering with two or more materials where at least one material is a soft material distributed to provide a less anisotropic response. Similar forms can be created, as previously mentioned, where multiple materials are used within the marker. One such embodiment is a single segmented marker with a constant cross section.

An additional benefit of this aspect of the invention is that the soft distribution or shape can be independent of the external form and cross sections which improve imaging visibility under ultrasound or X-ray can be created. Further examples of composite magnetic markers with decreased anisotropy include soft markers distributed on a collapsible stent-like structure specifically those that are self-expanding.

Figure 10:
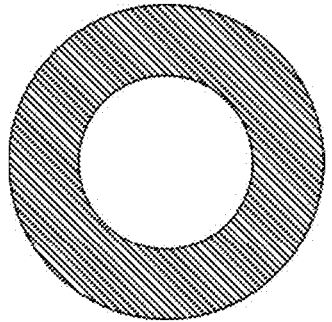
FIG. 10 is a diagram of the cross-section of an embodiment of the invention in the form of core and sheath.
Figure 11:
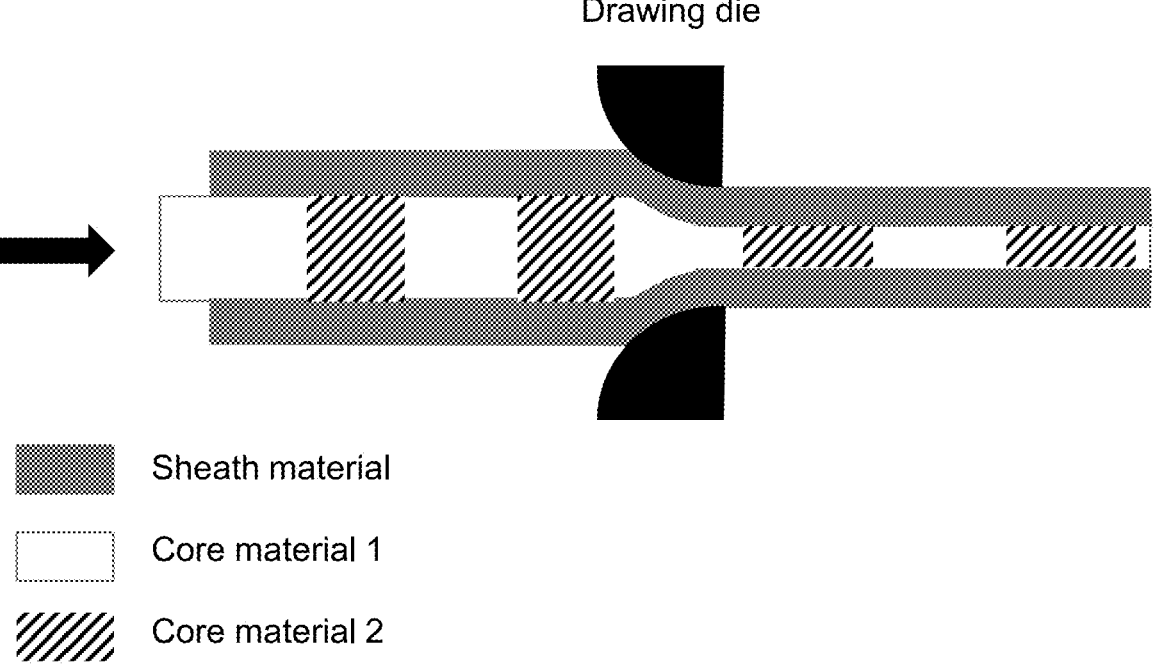
FIG. 11 is a diagram of the drawing of an embodiment of the invention having a sheath and multiple cores.

Additionally, in a cable or multi-wire strands (especially where twisted) embodiments include hollow versions where the individual wires are formed from different materials or formed from composite material, e.g., a core and a covering or sheath material where at least one or more of these are magnetically soft materials. A specific example of this is where the core or covering material is made from Nitinol or other shape memory material (including shape memory polymers) which is used to form the post deployment shape (FIG. 10). It is equally possible to create wire where a core produced from multiple materials covered by the sheathing material is produced and either used directly as the magnetic marker or subsequently used in cable or multi-strand forms (FIG. 11). The wires or one of the segments multi-core wires could also be used to provide improved X-ray visibility.

FIGS. 12(A) and (B) are examples of segmented marker (note: more or fewer segments are possible). The segmentation increases losses between sections in the axial direction and manages the opposing eddy current effect, reducing the anisotropy.

Figures 14A, 14B, 14C, 14D, 14E:
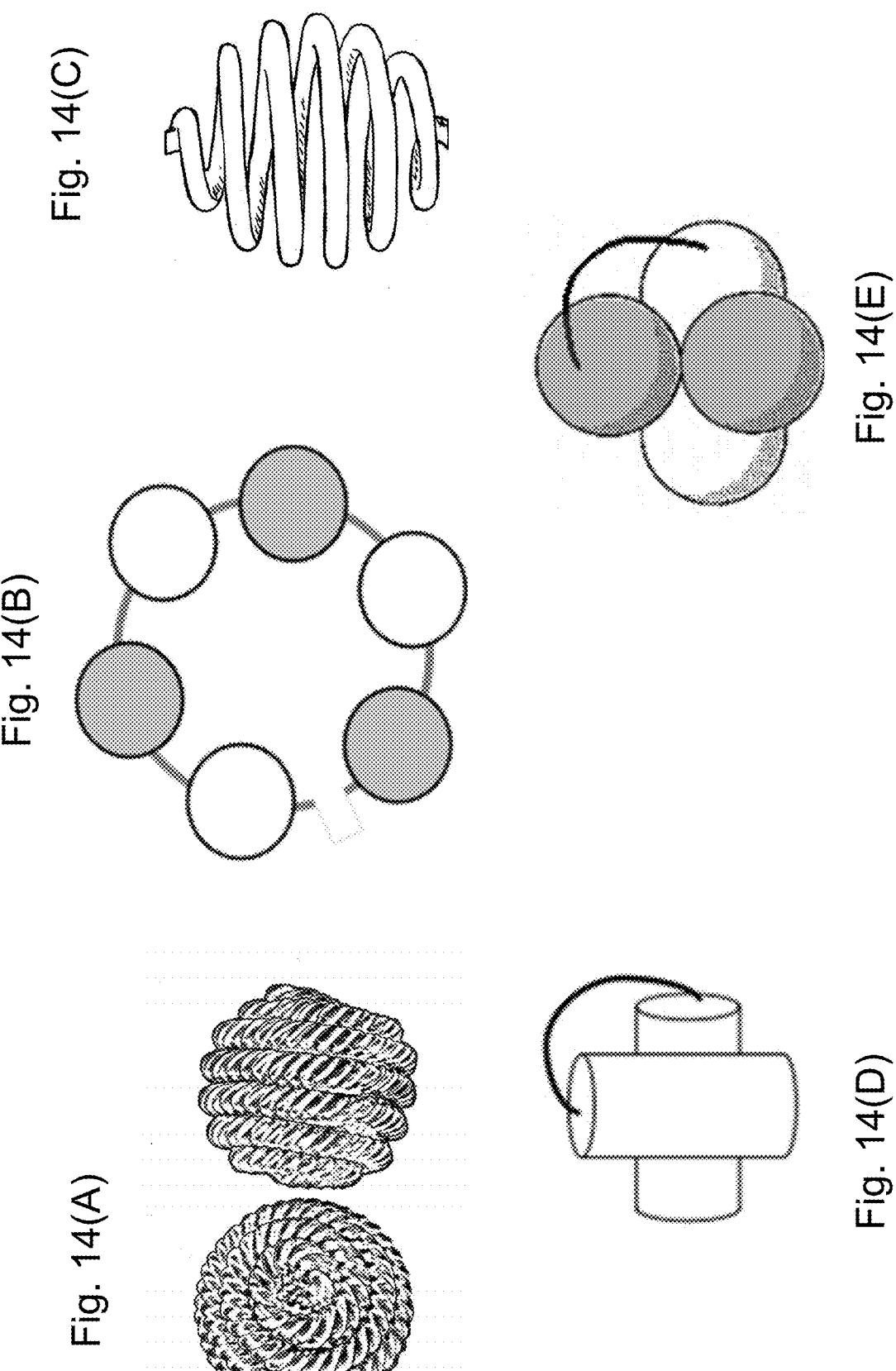
FIGS. 14(A)-(E) are diagrams of embodiments of the invention in the form of shaped markers with hinges made of various materials.

FIGS. 13(A) and (B) show examples of soft material (dark grey) that may be moulded into a shape that is independent Shaped markers with hinges of plastic/pre-stressed/shape memory in multiple materials with different magnetic properties are shown in FIGS. 14(A-E). These configurations improve the tailoring of the response in order to reduce the anisotropy by providing a substantially uniform response in any given axis of the marker. The multiple facets also provide superior ultrasound response.

In another aspect of the invention, a long thin marker is divided into a number of smaller markers. The multiple markers that are packed together prior to deployment have the same overall dimensions and material, and can be used to decrease the anisotropy relative to the overall dimensions of the material. For example, 3×2 mm long or 2×3 mm long or 6×1 mm long marker pieces have decreased anisotropy in comparison to 1×6 mm long marker of the same outer diameter. Surprisingly, this reduction in anisotropy occurs even when the segments align one behind each other in the same shape as an individual marker of the combined dimensions. (Table 3) For example, a single marker of dimension 5 mm in ferritic stainless steel gives an anisotropy ratio of 6.7. Two markers of the 3 mm markers in the same material give an anisotropy ratio of between 3.2 and 4.6 depending on relative orientations.

TABLE 3

| Marker | Pre-deployment dimensional ratio | Volume (mm³) | Signal Max | Signal Min | Anisotropy Ratio | Relative Limit of detection |
|---|---|---|---|---|---|---|
| Ferritic stainless steel multi-strand cable (0.91 mm in diameter) | 3.3 | 2.0 | 536 | 120 | 4.5 | 1.6 |
| Ferritic stainless steel multi-strand cable (0.91 mm in diameter) | 4.4 | 2.6 | 939 | 143 | 6.6 | 1.7 |
| Ferritic stainless steel multi-strand cable (0.91 mm in diameter) | 5.5 | 3.2 | 1212 | 182 | 6.7 | 2.0 |
| Two (2) Ferritic stainless steel multi-strand cable various configurations | 6.6 | 3.9 | 810-1091 | 240-254 | 3.2-4.6 | 1.7-1.9 | of the external shape of the marker (note: more than two materials could be used within the construction). Anisotropy is improved by providing more magnetic material in the transverse axis and reducing the opposing eddy current through combination of the materials selected. In one embodiment shown in FIG. 13(C), the magnetically soft core is formed from a material with a very high magnetic response such as a metallic glass such that sufficient magnetic response can be obtained from only a very small sphere of the material. The core is encased in a protective layer comprising a biocompatible coating or capsule, for example a titanium shell or a biocompatible polymer coating. Because the core is spherical, the ratio of magnetic anisotropy of susceptibility is close to 1.

Figure 15:
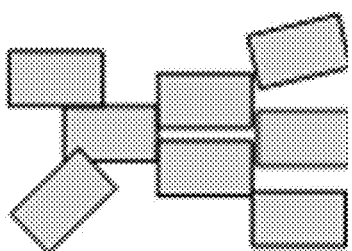
FIG. 15 is a diagram of an embodiment of the invention constructed by self assembly.

In a further specific example of this, a set of markers or magnetic particles produced from magnetically soft material can retain a small amount of magnetism. Once deployed into the patient, these magnetic particles can then self-assemble into an associated magnetic marker which possesses lower magnetic anisotropy of susceptibility. Multiple magnetically soft markers with a small magnetic remanence will self-assemble into an associated magnetic marker with a substantially uniform amount of material in every direction, thereby minimising anisotropy (FIG. 15). This small magnetic remanence can be overcome by the magnetic excitation of the exciting field of the magnetometer (or susceptometer) as described above. Table 4 shows the parameters of particles assembled by two types of magnetic compositions.

TABLE 4

| Marker | Pre-deployment dimensional ratio | Volume (mm³) | Signal Max | Signal Min | Anisotropy Ratio |
|---|---|---|---|---|---|
| MnZn-Ferrite (1.0 mm in diameter) | 3.5 | 5.9 | 981 | 166 | 5.9 |
| MnZn-Ferrite (0.75 mm in diameter) | 10 | 3.3 | 4120 | 202 | 20.4 |

TABLE 4-continued

| Marker | Pre-deployment dimensional ratio | Volume (mm³) | Signal Max | Signal Min | Anisotropy Ratio |
|---|---|---|---|---|---|
| Assembly of small markers as per FIG. 15 (0.75 mm in diameter MnZn-Ferrite) | 8.7 | 2.9 | 583 | 448 | 1.3 |

Figure 16:
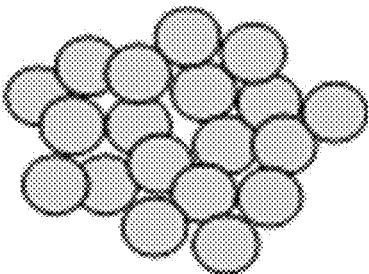
FIG. 16 is a diagram of an embodiment of the invention constructed by hydrophobic self-assembly.

In a further example of this, magnetically soft markers or particles encased within hydrophobic surfaces (nano-texturing via lotus effect, silica nano-coatings, EnBio CoBlast PTFE, Hydroxyapitite, carbon nanotube coatings, precipitate calcium carbide & fatty acid coating with polymer latex, manganese oxide polystyrene or zinc oxide polystyrene nano-composites) or spheres will pull together (self-assemble) on deployment into the patient. To minimise surface energy, this embodiment will form a close-packed shape such as a sphere or ellipsoid system which will have an improved magnetic anisotropy of susceptibility relative to the particles within the delivery system which will constrain in an elongated shape to be elongated. FIG. 16 depicts hydrophobic coated markers or particles which self-assemble, to minimise surface energy, into an associated magnetic marker with a substantially uniform amount of material in every direction minimising anisotropy.

Figure 17:
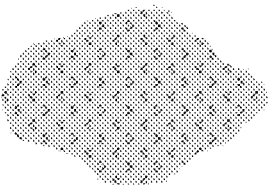
FIGS. 17(A) and (B) are diagrams of other embodiments of the invention constructed by self-assembly.
Figure 17:

In another aspect of the invention, small micromarkers or microparticles of a soft material can be suspended within a biocompatible matrix (FIGS. 17(A) and (B)). Control of the magnetic particle distribution, in a similar manner as discussed with respect to FIGS. 10-12, allows a decreased magnetic anisotropy of susceptibility as well as the independence from the outer form. It can also be used to ensure a set location and orientation between the magnetic markers.

In a further example of this for the case, by using a gel matrix with a suspension of magnetically soft particles and by sizing these particles appropriately, the gel and particles can be deployed through the deployment needle (FIG. 17(B)). The shape of the deployed gel and particles will be constrained only by the injection site (i.e. the tissue of a lesion) which is less in comparison to that of the needle. This gel can also set on injection making it less likely to migrate from its deployed location and easier to remove surgically if the tissue is being removed. The addition of other particles such as gold to provide additional radiopaque response for x-ray visualisation could be performed if required. For marker localization, the anisotropy should be less than or equal to 9, preferably less than or equal to 6, more preferably less than or equal to 3.

The present invention provides various ways of making magnetic markers with acceptable anisotropy while not affecting the case of delivery of the particles.

In another aspect of the invention, a method is provided for marking a soft tissue site of interest, such as the site of a tumor or benign lesion for example within the breast, lung, bowel/colon, rectum, prostate or other cancer affected organ, or a lymph node within the axilla or other nodal basin within the body. The method includes the steps of (i) inserting such a magnetic marker into tissue near the target lesion or site, and (ii) detecting such a marker using a susceptometer, and optionally (iii) surgically excising the target tissue around the marker. Preferably, the susceptometer detects the marker by providing a magnetic field in the region of the marker and measuring the induced magnetization in the marker.

Unless otherwise indicated, all numbers expressing lengths, widths, depths, or other dimensions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Any specific value may vary by 20%.

The terms "a," "an," "the," and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventor for carrying out the spirit of the present disclosure. Of course, variations on these described embodiments will become apparent to those of ordinary skill in the art upon reading the foregoing description. The inventor expects skilled artisans to employ such variations as appropriate, and the inventor intends for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. An implantable marker for marking a tissue site, the implantable marker comprising:

a structure having at least a portion thereof formed of at least one magnetic material with a mass susceptibility of greater than 0.05 m³/kg, wherein the structure is configured to change between a packed configuration and a deployed configuration, wherein the packed configuration has a first anisotropy of magnetic susceptibility, wherein the deployed configuration has a second anisotropy of magnetic susceptibility, wherein the first anisotropy of magnetic susceptibility is greater than the second anisotropy of magnetic susceptibility.

2. The implantable magnetic marker of claim 1, wherein the first anisotropy of magnetic susceptibility is less than or equal to 5.

3. The implantable magnetic marker of claim 1, wherein the first anisotropy of magnetic susceptibility is greater than 5.

4. The implantable magnetic marker of claim 1, wherein the first anisotropy of magnetic susceptibility is less than or equal to 9.

5. The implantable magnetic marker of claim 1, wherein the first anisotropy of magnetic susceptibility is greater than or equal to 9.

6. The implantable magnetic marker of claim 1, wherein the at least one magnetic material has a magnetic coercivity of less than about 79.6 kAm-1 (1000 Oe).

7. The implantable magnetic marker of claim 1, wherein the at least one magnetic material has a magnetic coercivity of less than about 500 Oe.

8. The implantable magnetic marker of claim 1, wherein the at least one magnetic material has a magnetic coercivity of less than about 100 Oe.

9. The marker of claim 1, wherein the structure comprises a first segment and a second segment.

10. The marker of claim 9, wherein the first segment comprises a solid material, wherein the second segment comprises a second material.

11. The marker of claim 1, wherein the deployed configuration has one or more shapes or combinations of one or more shapes.

12. The marker of claim 11, wherein the one or more shapes are selected from the group consisting of: a bead, a dumbbell, dumbbell-like forms, a cable, a ball of yarn, a cylinder, a wire, and a multi-stranded cable.

13. The marker of claim 1, wherein the structure is deployable using a needle.

14. A method comprising:

providing an implantable marker for marking a tissue site in a packed configuration, wherein the packed configuration has a first anisotropy of magnetic susceptibility; and changing the packed configuration of the implantable marker to a deployed configuration, wherein the deployed configuration has a second anisotropy of magnetic susceptibility, wherein the first anisotropy of magnetic susceptibility is greater than the second anisotropy of magnetic susceptibility, wherein the implantable marker comprises at least one magnetic material with a mass susceptibility of greater than 0.05 m³/kg.

15. The method of claim 14 further comprising localizing the implantable marker after implantation, using a hand-held probe, wherein the implantable marker is in the deployed configuration.

16. The method of claim 14, wherein the first anisotropy of magnetic susceptibility is less than or equal to 5.

17. The method of claim 14, wherein the first anisotropy of magnetic susceptibility is greater than 5.

18. The method of claim 14, wherein the first anisotropy of magnetic susceptibility is less than or equal to 9.

19. The method of claim 14, wherein the first anisotropy of magnetic susceptibility is greater than or equal to 9.

* * * * *